(12) United States Patent
Polk et al.

(10) Patent No.: US 9,682,120 B2
(45) Date of Patent: Jun. 20, 2017

(54) COMPOSITIONS AND METHODS FOR THE TREATMENT OF DISORDERS INVOLVING EPITHELIAL CELL APOPTOSIS

(71) Applicant: Vanderbilt University, Nashville, TN (US)

(72) Inventors: D. Brent Polk, Nashville, TN (US); Fang Yan, Franklin, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 0 days.

(21) Appl. No.: 14/833,611

(22) Filed: Aug. 24, 2015

(65) Prior Publication Data
US 2016/0038564 A1 Feb. 11, 2016

Related U.S. Application Data

(62) Division of application No. 11/923,397, filed on Oct. 24, 2007, now Pat. No. 9,133,249.

(60) Provisional application No. 60/862,715, filed on Oct. 24, 2006.

(51) Int. Cl.
  *A61K 38/16* (2006.01)
  *C07K 14/195* (2006.01)
  *A61K 38/00* (2006.01)

(52) U.S. Cl.
  CPC .......... *A61K 38/164* (2013.01); *C07K 14/195* (2013.01); *A61K 38/00* (2013.01)

(58) Field of Classification Search
None
See application file for complete search history.

(56) References Cited

PUBLICATIONS

Bowie et al. (Science, 1990, 247:1306-1310).*
Burgess et al. (J. Cell Biol. 111:2129-2138, 1990).*
Lazar et al. (Mol. Cell. Biol., 8:1247-1252, 1988).*
"Cell wall-associated hydrolase," EBI accession No. UNIPROT:QO3CD1, Nov. 14, 2006.
"Surface antigen," EBI accession No. UNIPROT:QO3D36, Nov. 14, 2006.
Amaravadi and Thompson, "The survival kinases Akt and Pim as potential pharmacological targets," *J. Clin. Invest.*, 115:2618-2624, 2005.
Apostolou et al., "Good adhesion properties of probiotics: a potential risk for bacteremia?," *FEMS Immunol. Med. Microbiol.*, 31:35-39, 2001.
Borody et al., "Treatment of ulcerative colitis using fecal bacteriotherapy," *J. Clin. Gastroenterol.*, 37:42-47, 2003.
Bousvaros et al., "A randomized, double-blind trial of Lactobacillus GG versus placebo in addition to standard maintenance therapy for children with Crohn's disease," *Inflamm. Bowel Dis.*, 11:833-839, 2005.
Dieleman et al., "Lactobacillus GG prevents recurrence of colitis in HLA-B27 transgenic rats after antibiotic treatment," *Gut.*, 52:370-376, 2003.
Dotan et al., "Probiotics in inflammatory bowel disease: possible mechanisms of action," *Curr. Opin. Gastroenterol.*, 21:426-430, 2005.
Knodler et al., "The *Salmonella* effector protein SopB protects epithelial cells from apoptosis by sustained activation of Akt," *J. Biol. Chem.*, 280:9058-9064, 2005.
Mack et al., "Extracellular MUC3 mucin secretion follows adherence of *Lactobacillus* strains to intestinal epithelial cells in vitro," *Gut.*, 52:827-833, 2003.
Office Communication issued in U.S. Appl. No. 11/923,397, dated Nov. 12, 2010.
Office Communication issued in U.S. Appl. No. 11/923,397, dated Apr. 29, 2014.
Office Communication issued in U.S. Appl. No. 11/923,397, dated Nov. 24, 2014.
Otte and Podolsky, "Functional modulation of enterocytes by gram-positive and gram-negative microorganisms," *Am. J. Physiol. Gastrointest. Liver Physiol.*, 286:G613-G626, 2004.
PCT International Search Report and Written Opinion, issued in International Application No. PCT/US2007/082352, dated Mar. 6, 2008.
Resta-Lenert and Barrett, "Live probiotics protect intestinal epithelial cells from the effects of infection with enteroinvasive *Escherichia coli* (EIEC).," *Gut.*, 52:988-997, 2003.
Resta-Lenert and Barrett, "Probiotics and commensals reverse TNF-alpha- and IFN-gamma-induced dysfunction in human intestinal epithelial cells," *Gastroenterology*, 130:731-746, 2006.
Sartor, "Therapeutic manipulation of the enteric microflora in inflammatory bowel diseases: antibiotics, probiotics, and prebiotics," *Gastroenterology*, 126:1620-1633, 2004.
Schultz et al., "Lactobacillus GG in inducing and maintaining remission of Crohn's disease," *BMC Gastroenterol.*, 4:5, 2004.
Sheng et al., Phosphatidylinositol 3-kinase mediates proliferative signals in intestinal epithelial cells, *Gut.*, 52:1472-1478, 2003.
Tao et al., "Soluble factors from Lactobacillus GG activate MAPKs and induce cytoprotective heat shock proteins in intestinal epithelial cells," *Am. J. Physiol. Cell Physiol.*, 290:C1018-C1030, 2006.
Tien et al., "Anti-inflammatory effect of *Lactobacillus casei* on Shigella-infected human cells," *J. Immunol.*, 176:1228-1237, 2006.
Trencia et al., "Protein kinase B/Akt binds and phosphorylates PED/PEA-15, stabilizing its antiapoptotic action," *Mol. Cell Biol.*, 23:4511-4521, 2003.
Xu et al., "A genomic view of the human-Bacteroides thetaiotaomicron symbiosis," *Science*, 299:2074-2076, 2003.
Yan and Polk, "Commensal bacteria in the gut: learning who our friends are," *Curr. Opin. Gastroenterol.*, 20:565-571, 2004.
Yan and Polk, "Probiotic bacterium prevents cytokine-induced apoptosis in intestinal epithelial cells," *J. Biol. Chem.*, 277:50959-50965, 2002.

(Continued)

*Primary Examiner* — Brian J Gangle
(74) *Attorney, Agent, or Firm* — Parker Highlander PLLC

(57) ABSTRACT

The present invention provides therapeutic and prophylactic compositions for use in treating and preventing disorders involved epithelial cell apoptosis, such as gastrointestinal disorders (e.g., inflammatory bowel disease, Crohn's disease or ulcerative colitis) in a subject, such as a human patient.

16 Claims, 10 Drawing Sheets

(56) References Cited

PUBLICATIONS

Yan and Polk, "Probiotics as functional food in the treatment of diarrhea," *Curr. Opin. Clin. Nutr. Metab. Care*, 9:717-721, 2006.
Yan et al., "Kinase suppressor of Ras determines survival of intestinal epithelial cells exposed to tumor necrosis factor," *Cancer Res.*, 61:8668-8675, 2001.
Yan et al., "Kinase suppressor of Ras-1 protects intestinal epithelium from cytokine-mediated apoptosis during inflammation," *J. Clin. Invest.*, 114:1272-1280, 2004.
Yan et al., "Soluble proteins produced by probiotic bacteria regulate intestinal epithelial cell survival and growth," *Gasttroenterology*, 132:562-575, 2007.
Zhang et al., "Staphylococcal lipoteichoic acid inhibits delayed-type hypersensitivity reactions via the platelet-activating factor receptor," *J. Clin. Invest.*, 115:2855-2861, 2005.
GeneBank Accession No. COG0791 2004.
GeneBank Accession No. COG3883 2005.
Gill et al., "Enhancement of natural and acquired immunity by Lactobacillus rhamnosus (HN001), Lactobacillus acidophilus (HN017) and Bifidobacterium lactis (HN019).," *Br. J. Nutr.*, 83:167-176, 2000.
Goetz et al., "Comparison of selected analytical techniques for protein sizing, quantitation and molecular weight determination", *Biochemical and Biophysical Methods*, 60: 281-293, 2004.
Hanada et al., "Structure, regulation and function of PKB/AKT—a major therapeutic target," *Biochim. Biophys. Acta.*, 1697:3-16, 2004.
Hooper et al., "Molecular analysis of commensal host-microbial relationships in the intestine," *Science*, 291:881-884, 2001.
Ichikawa et al., "Probiotic bacteria stimulate gut epithelial cell proliferation in rat," *Dig. Dis. Sci.*, 44:2119-2123, 1999.
Kelly et al., "Commensal anaerobic gut bacteria attenuate inflammation by regulating nuclear-cytoplasmic shuttling of PPAR-gamma and Re1A," *Nat. Immunol.*, 5:104-112, 2004.
Knodler et al.,"The Salmonella effector protein SopB protects epithelial cells from apoptosis by sustained activation of Akt," *J. Biol. Chem.*, 280:9058-9064, 2005.
Land et al., "Lactobacillus sepsis associated with probiotic therapy," *Pediatrics*, 115:178-181, 2005.
Mack et al. "Extracellular MUC3 mucin secretion follows adherence of Lactobacillus , strains to intestinal epithelial cells in vitro," *Gut.*, 52:827-833, 2003.
Macpherson and Uhr, "Induction of protective IgA by intestinal dendritic cells carrying commensal bacteria," *Science*, 303:1662-1665, 2004.
Mimura et al., "Once daily high dose probiotic therapy (VSL#3) for maintaining remission in recurrent or refractory pouchitis," *Gut.*, 53:108-114, 2004.
Neish, "Molecular aspects of intestinal epithelial cell-bacterial interactions that determine the development of intestinal inflammation," *Inflamm. Bowel Dis.*, 10:159-168, 2004.
Office Communication issued in U.S. Appl. No. 11/923,397, dated Dec. 29, 2009.

\* cited by examiner

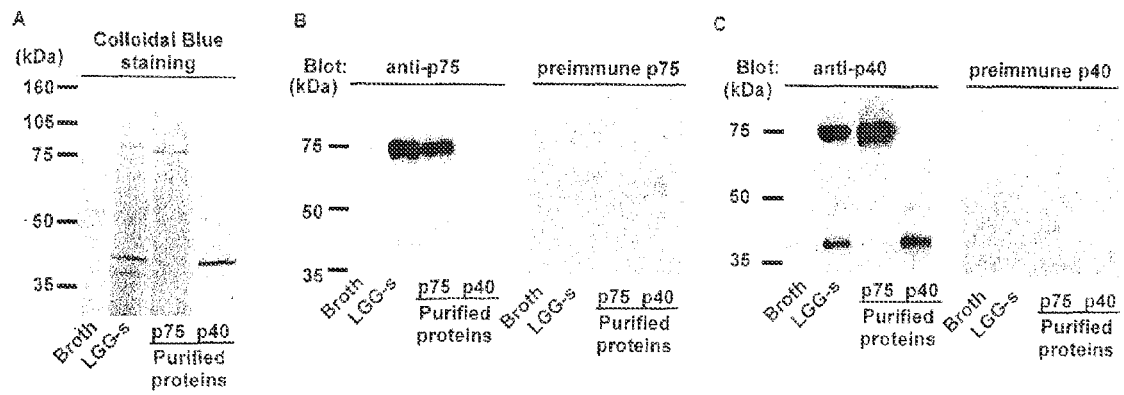

D
Full-length p40 protein sequence (412 aa)

MKFNKAMITLVAAVTLAGSVSALTPVFADTSASIASNKSETNDLLKQIEAANTEVINLNKQIDAKNGEISDATA
KISATDAKIASLSGEITAAQKNVAARKNNLKDQLISLQKKAGSSVSGNVYIDFVLNSQSLSDLIARTMTVGKLS
QASKDALDAVTVAKDKLAALKSEQETARQTLVSTKASLETQKSQLETLQKTASDKQDALNKEIADHKDELVA
LQSQFAQEQSEAAKATQAALKTAAASTASSSTSSTSNKSANSSVLSTGTSSTNTSSNSGASSTVISSNTASG
SGSHADYSGSGNTYPWGQCTWYVKSVASWAGNGWGNGAEWGASAAAAGFTVNHTPAAGSIIVFAAGQS
VGGQWTADGSYGHVAYVQSVSGDSVTITQGGMGFSSPTGPNTQTISGASSYV

Partial p75 protein sequence (first 496 aa)

MVDSKKVLSVTAGFVGAAGLAALATGANTVSASTGTVSYKSGATTVWNSPSWHQVKRYVTFGDTVQLLGK
TVDQNGATWYKVGDNQWIPELYLNVAGKTATVETPSSAASQTAVSQAPASQAPTSQAPATQTPAAPQTDT
QTANTQLYVKNIGSAVTVWTTPAYTHATGQYLEGSQTLTAVAQQQANGETWYRLANGGYVPARLLHNTSG
CNTTTAAPQSNEASVASTNTNAANDSAAASSAAASQAAASSAAASTAAANAAVASANATASQAAASEAAAS
QAAASQAAASQAAASQAAASQAAASQAAASQAAASQAAASQAAANAAQQAPANQANVTTTQVNA
NQAQQQTATATPAVNTSNQTAAVSASRQAKIQAVIAIAEQQVGKPYVWGGKGPNSFDCSGLMYYAFLNGA
GVNIGGWTVPQESSGTQVSLSALQPGDLLFWGSHGSTYHVALYIGGGTMIQAPQPGENVKYTALAYFMPD
LLFVLH

FIG. 1A-D

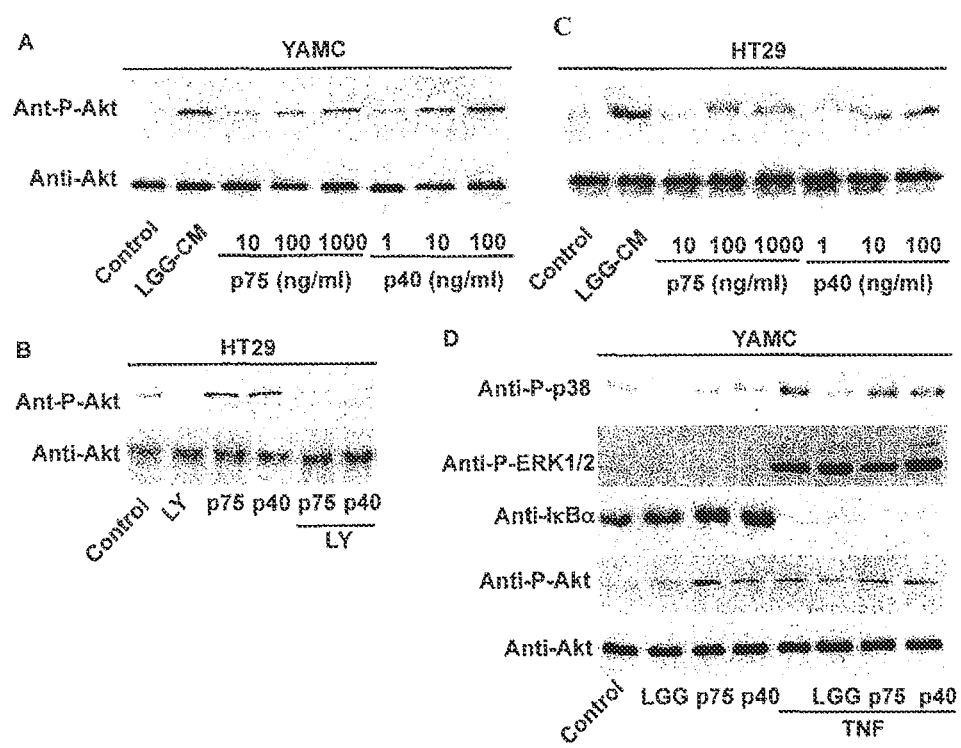
FIG. 2A–D

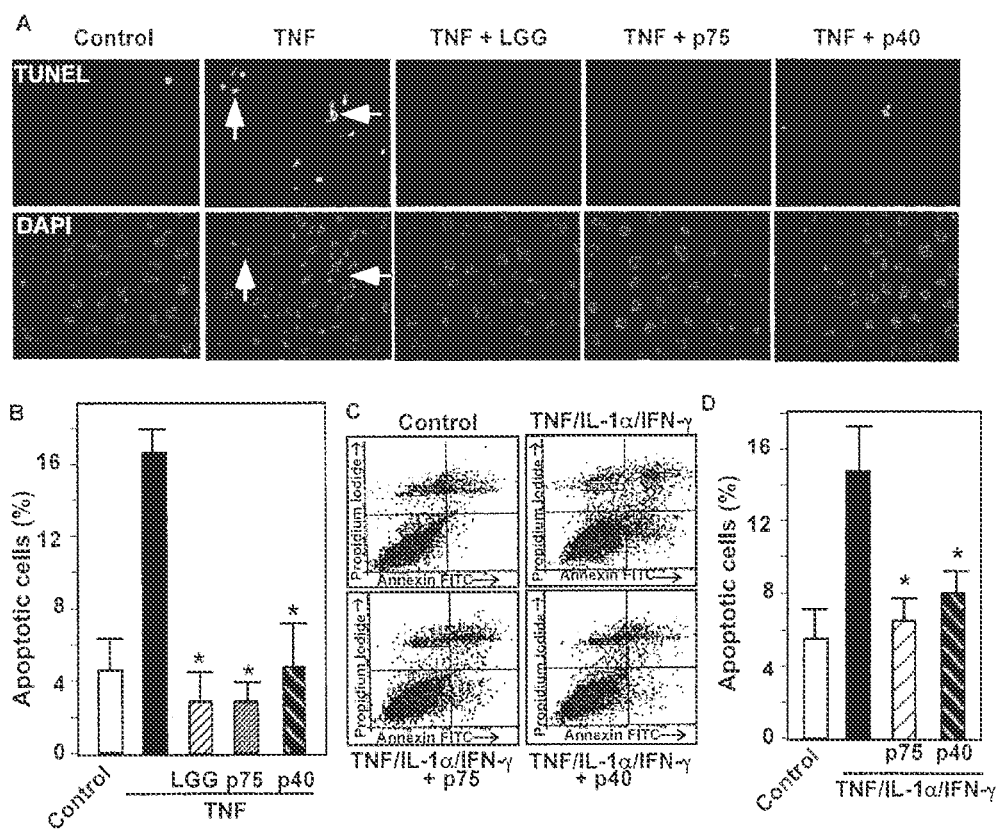
FIG. 3A-D

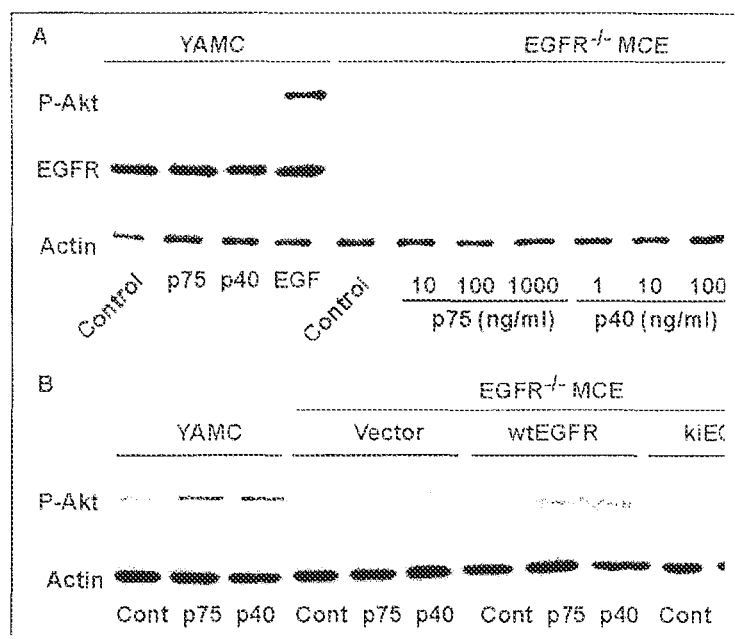
FIG. 10A-B

COMPOSITIONS AND METHODS FOR THE TREATMENT OF DISORDERS INVOLVING EPITHELIAL CELL APOPTOSIS

CROSS-REFERENCE TO RELATED APPLICATIONS

The present application is a divisional of U.S. application Ser. No. 11/923,397, filed Oct. 24, 2007, which claims benefit of priority to U.S. Provisional Application Ser. No. 60/862,715, filed Oct. 24, 2006. The entire contents of each of the applications referenced above are hereby incorporated by reference.

STATEMENT OF FEDERAL FUNDING

This invention was made with government support under DK 065744 and DK 58404 awarded by the National Institute of Health. The government has certain rights in the invention.

INCORPORATION OF SEQUENCE LISTING (a) The sequence listing that is contained in the file named "VBLTP0100USD1_ST25.txt", which is 12 KB (as measured in Microsoft Windows®) and was created on Aug. 24, 2015, is filed herewith by electronic submission and is incorporated by reference herein.

BACKGROUND OF THE INVENTION

1. Field of the Invention

The present invention relates generally to the fields of cell biology, biochemistry and medicine. More particularly, it concerns use of soluble factors produced by probiotic bacteria for the inhibition of epithelial cell apoptosis, including gastrointestinal disorders.

2. Description of Related Art

Inflammatory bowel diseases (IBD) are characterized by increased production of inflammatory cytokines, epithelial cell apoptosis, and immune cell infiltration, leading to disruption of the intestinal epithelial integrity (Sartor, 2002). Therefore, remission of these disorders requires both decreased apoptosis and restitution of the damaged epithelium. Recent studies reveal several potential therapeutic approaches to induce restitution of the damaged epithelium. Growth factors (El-Assal and Besner, 2005; Matsuura et al., 2005; McCole et al., 2005; Sinha et al., 2003) and cytokines (Marini et al., 2003; Zeissig et al., 2004) have been reported to modulate these processes by regulating proliferation (Matsuura et al., 2005), migration (El-Assal and Besner, 2005), and apoptosis (Marini et al., 2003; Zeissig et al., 2004).

Increasing evidence suggests some commensal bacteria enhance intestinal epithelial homeostasis and barrier integrity. Indeed, commensal bacteria regulate a number of host processes, including nutrition, development, and immune responses, that are relevant for both health and disease (Yan and Pol, 2004). Therefore, manipulation of intestinal bacterial flora has been used as an alternative health approach for disease prevention and treatment (Sartor, 2004). Living microorganisms in the intestinal tract which benefit the host are termed probiotics (Lilly and Stillwell, 1965). Recent studies indicate that some *Lactobacillus* species function as probiotics and induce sustained remission in ulcerative colitis and pouchitis (Borody et al., 2003; Dieleman et al., 2003; Mimura et al., 2004; Schultz et al., 2004). *Lactobacillus rhamnosus* GG (LGG), a bacterium used in the production of yogurt, is one of the best-studied *Lactobacillus* strains in clinical trials for IBD.

The presumed first target of probiotic actions is the intestinal epithelial cell. Probiotic bacteria stimulate several intestinal epithelial cell protective responses, including enhancement of epithelial barrier function (Resta-Lenert and Barrett, 2003; Resta-Lenert and Barrett, 2006), mucin synthesis and secretion (Mack et al., 2003; Otte and Podolsky, 2004), inhibition of enteropathogenic *E. coli* binding (Mack et al., 2003), and cell survival (Yan and Polk, 2002). However, the mechanisms regulating epithelial responses to probiotics are complex and mostly unknown. The inventors have used LGG to investigate molecular mechanisms by which probiotics regulate intestinal epithelial cells, and previously reported that LGG prevents cytokine-induced apoptosis in both human and mouse intestinal epithelial cells through activating Akt and inhibiting p38 mitogen activated protein kinase (MAPK) activation (Yan and Polk, 2002). Akt plays a central role in promoting cell survival by inactivation of several proapoptotic pathways, including BAD, caspase 9 and caspase 3, and stimulating cell proliferation by activation of cell cycle regulators, such as cyclin/CDK (Amaravadi and Thompson, 2005; Hanada et al., 2004). They have further reported that soluble factors recovered from LGG culture broth supernatant (LGG-s) activate Akt in a phosphatidylinositol-3'-kinase (PI3K)-dependent manner and prevent cytokine-mediated apoptosis (Yan and Polk, 2002). One recent report has shown that soluble factors present in LGG conditioned-medium (LGG-CM) induce cytoprotective heat shock protein synthesis in intestinal epithelial cells (Tao et al., 2006). However, to the inventors' knowledge, the specific components of LGG-s that promote intestinal epithelial health have not been identified. Therefore, purification and characterization of LGG-derived soluble proteins that regulate intestinal epithelial cell proliferation and survival is needed.

SUMMARY OF THE INVENTION

Thus, in accordance with the present invention, there is provided a purified and isolated protein having the properties of (a) stimulating PI3K-dependent Akt activation; (b) inhibiting cytokine-induced epithelial cell apoptosis; (c) promoting epithelial cell growth; and (d) an apparent molecular weight of 40 or 75 kDa as determined by SDS-PAGE. The 40 kD protein may have the sequence of SEQ ID NO:1, and the 70 kD protein may have the sequence of SEQ ID NO:3. In another embodiment, there is provided a pharmaceutical composition of the above proteins dispersed in a pharmaceutically acceptable buffer, diluent or excipient.

In yet another embodiment, there is provided an isolated and purified nucleic acid segment encoding a protein having the sequence of SEQ ID NO:1 or 3. The nucleic acid segment may comprise the sequence of SEQ ID NO:2 or 4. The nucleic acid segment may further comprise a promoter that directs the transcription of said nucleic acid segment. The promoter may be heterologous to SEQ ID NO:1 or 3. The nucleic acid segment may further comprise a replicable vector, such as a plasmid or a viral vector, including a baculovirus vector.

In still yet another embodiment, there is provided a host cell comprising an isolated and purified nucleic acid segment encoding a protein having the sequence of SEQ ID NO:1 or 3. The host cell may be a bacterial cell, such as a *Lactobaccillus* cell, or a eukaryotic cell, such as a yeast cell or an insect cell.

Also provided are an oligonucleotide segment of 15 to 50 bases comprising at least 15 consecutive bases of SEQ ID NO:2 or 4. The oligonucleotide segment may be 15, 16, 17, 18, 19, 20, 21, 22, 23, 24, 25, 30, 35, 40, 45 or 50 bases in length, and the oligonucleotide segment may comprise 15, 16, 17, 18, 19, 20, 21, 22, 23, 24, 25, 30, 35, 40, 45 or 50 consecutive bases of SEQ ID NO:2 or 4. The oligonucleotide segment may be single-stranded or double-stranded, and may be a DNA segment. The oliogonucleotide segment may be labeled with a detectable label.

In still a further embodiment, there is provided a method of inhibiting cytokine-induced epithelial cell apoptosis and/or promoting epithelial cell growth in a subject comprising administering to said subject a pharmaceutical composition comprising (i) a purified and isolated protein having the properties of (a) stimulates PI3K-dependent Akt activation; (b) inhibits cytokine-induced epithelial cell apoptosis; (c) promotes epithelial cell growth; (d) an apparent molecular weight of 40 or 75 kDa as determined by SDS-PAGE, and (ii) a pharmaceutically acceptable buffer, diluent or excipient. The protein may have the sequence of SEQ ID NO:1 or SEQ ID NO:3. The subject may be a human, a rat, a mouse, a sheep, a dog, a cat, or a rabbit. The subject may suffer from a gastrointestinal infection, such as cholera, rotavirus infection or infection by enterotoxigenic *E. coli*. The subject may suffer from a gastrointestinal disorder, such as inflammatory bowel disease, irritable bowel syndrome, Crohn's disease, necrotizing enterocolitis, ulcerative colitis, celiac disease, HIV enteropathy, *Helicobacter* gastritis or NSAID-enteropathy/enteritis. The endothelial cell may be comprised within skin tissue, corneal tissue or lung tissue, within an inflamed tissue, within heart tissue, muscle or a joint, and/or within cytokine-injured tissue.

In yet another embodiment, there is provided a method of preventing or treating a gastrointestinal disease in a subject comprising administering to said subject a pharmaceutical composition comprising (i) a purified and isolated protein having the properties of (a) stimulates PI3K-dependent Akt activation; (b) inhibits cytokine-induced epithelial cell apoptosis; (c) promotes epithelial cell growth; (d) an apparent molecular weight of 40 or 75 kDa as determined by SDS-PAGE, and (ii) a pharmaceutically acceptable buffer, diluent or excipient.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed in this specification can be implemented with respect to any method or composition of the invention, and vice versa. Furthermore, compositions and kits of the invention can be used to achieve methods of the invention.

Throughout this application, the term "about" is used to indicate that a value includes the inherent variation of error for the device, the method being employed to determine the value, or the variation that exists among the study subjects.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-D—Purification and sequencing of p75 and p40 purified from LGG-s. Filtered LGG culture supernatant was loaded onto a cation exchange column. Proteins bound to exchange media were eluted using Tris buffer containing sequential concentrations of NaCl (100-800 mM). Eluted proteins were separated by SDS-PAGE and stained with Colloidal Blue Staining Kit (FIG. 1A, lanes 3 and 4). Proteins present in concentrated fractions of broth and LGG-s using a 5 kDa cut-off filter are shown (FIG. 1A, lanes 1 and 2, respectively). Polyclonal antibodies against p75 or p40 were generated as detailed in methods, and used in Western blot analysis (FIG. 1B and FIG. 1C). N-terminal sequences (bold) and internal peptide sequences (underline) of p75 and p40 were detected by Edman degradation or MALDI-TOF/MS/MS and LC/MS/MS analysis, respectively (FIG. 1D). LGG genetic sequences encoding p75 and p40 were determined as described in the Methods, and predicted amino acid sequences were deduced from the nucleotide sequences (FIG. 1D) (SEQ ID NOS: 4 and 2, respectively).

FIGS. 2A-D—p75 and p40 stimulate Akt activation in mouse and human colon epithelial cells. Young adult mouse colon (YAMC) (FIG. 2A and FIG. 2D) and HT29 (FIG. 2B and FIG. 2C) cells were treated with purified p75 or p40 at the indicated concentrations for 2 hours in the presence or absence of 30-minute pretreatment of PI3K inhibitor, LY294002 (10 μM, FIG. 2C). Akt, p38, ERK1/2 MAPK activation and IκBα degradation were detected by Western blot analysis of cellular lysates with indicated antibodies. Data in this Figure are representative of five separate experiments.

FIGS. 3A-D—p75 and p40 inhibit cytokine-induced apoptosis in intestinal epithelial cells. KSR$^{-/-}$MCE cells (FIG. 3A and FIG. 3B) or HT29 cells (FIG. 3C and FIG. 3D) were treated with tumor necrosis factor (TNF) (100 ng/ml) for 6 hours, or the "cytokine cocktail" combination of TNF (100 ng/ml), IL-1α (10 ng/ml) and γ-IFN (100 ng/ml) for 16 hours, respectively, in the presence or absence of 1-hour pretreatment with viable LGG, p75 (100 ng/ml) or p40 (10 ng/ml). LGG, p75 and p40 were maintained during the entire course of cytokine treatment in all experiments shown in this paper. KSR$^{-/-}$MCE cells were fixed for TUNEL with apoptotic nuclei labeled with FITC and DAPI staining (FIG. 3A). FITC and DAPI labeled images were taken from the same field. Arrows indicate representative apoptotic nuclei. The percentage of cells undergoing apoptosis is shown (FIG. 3B). HT29 cells were dissociated and stained with Annxin V-FITC and propidium iodide, and analyzed by flow cytometry (FIG. 3C). Results were shown as density plots with Annxin V-FITC vs propidium iodide (FIG. 3D). Viable cells have low Annexin V-FITC and low propidium iodide staining (lower-left quadrant), early apoptotic cells have high Annexin V-FITC and low propidium iodide staining (lower-right quadrant), late apoptotic cells have high Annexin V-FITC and high propidium iodide staining (upper-right quadrant), necrotic cells have low Annexin V-FITC and high propidium iodide staining (upper-left quadrant). The early apoptotic cell populations in the lower-right quadrant are shown in (FIG. 3D). *, $p<0.01$ compared to TNF (B) or the "cytokine cocktail" (FIG. 3D), respectively. Experiments in this figure were performed on at least three separate occasions.

FIGS. 10A-B—EGF receptor mediates p75 and p40 activation of Akt. YAMC and EGFR$^{-/-}$ MCE cells with re-expression of wtEGFR, kiEGFR or vector only were treated with p75 (100 ng/ml) or p40 (10 ng/ml) or as indicated in FIG. 10A) for 1 hr. Akt activation was detected by Western blot analysis of cellular lysates using anti-Akt Ser473 (P-Akt) antibody. EGFR and Actin levels were detected using anti-EGFR and anti-Actin antibodies, respectively.

DESCRIPTION OF ILLUSTRATIVE EMBODIMENTS

Figure 4:
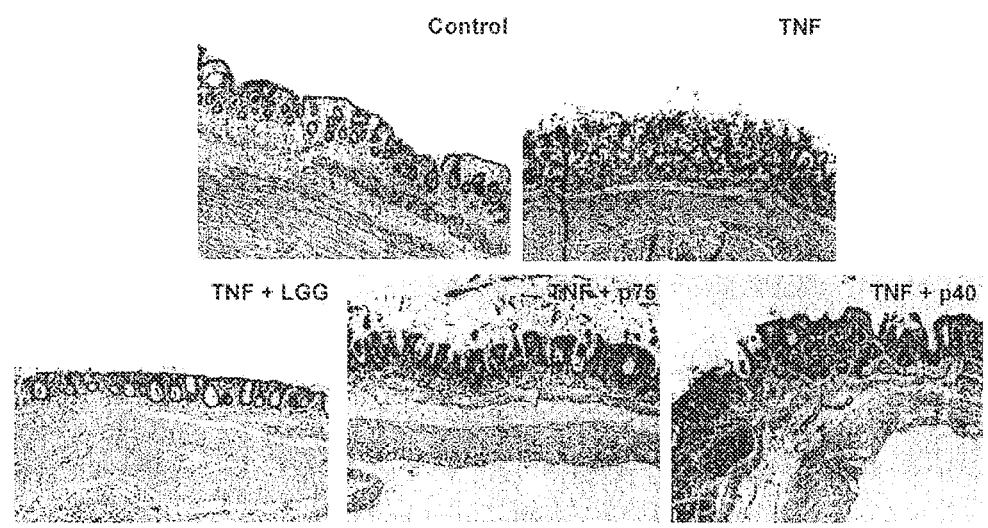
FIG. 4—p75 and p40 rescue TNF-induced epithelial damage in cultured mouse colon explants. Colon explants derived from 6-8 week old C57BL/6 mice were cultured in DMEM containing 0.5% FBS and treated with TNF (100 ng/ml) for 24 hours in the presence or absence of LGG, p75 (100 ng/ml) or p40 (10 ng/ml). Paraffin-embedded tissue sections were stained with hematoxylin and eosin for light microscopic assessment of epithelial damage (10× magnification). Images shown are representative of seven mice in each group.

Probiotics have recently received clinical attention for their potential to prevent and/or treat IBD (Sartor, 2004). The inventors previously showed LGG-derived soluble factors regulate cell survival signaling and inhibit cytokine-induced apoptosis in intestinal epithelial cells (Yan and Polk, 2002). Here, the inventors report purification of two LGG-derived soluble proteins (p75 and p40) and demonstrate that both of these proteins suppress cytokine-induced colon epithelial apoptosis and injury. These findings provide a molecular basis for therapeutic application of probiotic bacterial products for inflammation-mediated intestinal disorders. In vivo studies applying p75 and p40 to regulate intestinal inflammatory responses in animal models should demonstrate the feasibility of their use as novel treatments for IBD.

Although LGG has been shown to induce remission and prevent recurrence of IBD in patients (Schultz et al., 2004) and in animal models of colitis (Dieleman et al., 2003), a clinical trial designed to test the efficacy of LGG as an adjunct to standard therapy in children with Crohn's disease showed no beneficial effect of LGG in maintaining remission (Bousvaros et al., 2005). These results emphasize a current problem regarding the use of probiotic therapy, namely the difficulty determining the bioavailability of bacteria in the gastrointestinal tract. In addition, use of live probiotic bacteria raises concerns because of several cases of bacteremia associated with probiotic therapy in very young (Land et al., 2005) and immuno-compromised patients (Apostolou et al., 2001). Therefore, one approach to address these questions may be to use probiotic bacterial-derived proteins as novel therapeutic agents for treatment of IBD and other inflammation-related disorders.

Commensal bacteria engage in active cross-talk with the intestinal epithelium to promote epithelial development (Hooper et al., 2001), facilitate nutrient digestion and uptake by epithelial cells (Xu et al., 2003), and exert protective roles on intestinal inflammation (Dotan and Rachmilewitz, 2005). The known mechanisms for these functions include enhancing production of anti-inflammatory cytokines, blocking production of pro-inflammatory cytokines, antagonism to pathogenic bacteria (Otte and Podolsky, 2004), increasing secretory-IgA production (Macpherson and Uhr, 2004) and maintaining barrier function (Resta-Lenert and Barrett, 2003; Resta-Lenert and Barrett, 2006. However, the specific bacterial factors which attenuate epithelial inflammatory responses remain unclear. The inventors provide two lines of evidence to support the importance of p75 and p40 in regulating intestinal homeostasis. First, they show that the Lactobacillus strain, Lactobacillus acidophilus, whose culture supernatants do not contain p75 and p40, requires bacterial-cell contact for both Akt activation and suppression of cytokine-induced apoptosis (FIGS. 8A-D). Consistent with these findings, Barrett's group reported Lactobacillus acidophilus regulation of epithelial barrier function depends on bacterial-cell interaction (Resta-Lenert and Barrett, 2003). Second, immunodepletion experiments show that loss of p75 and p40 from LGG-CM eliminates LGG-CM's anti-apoptotic effects on colon epithelial cells (FIGS. 7A-E).

Figure 8:
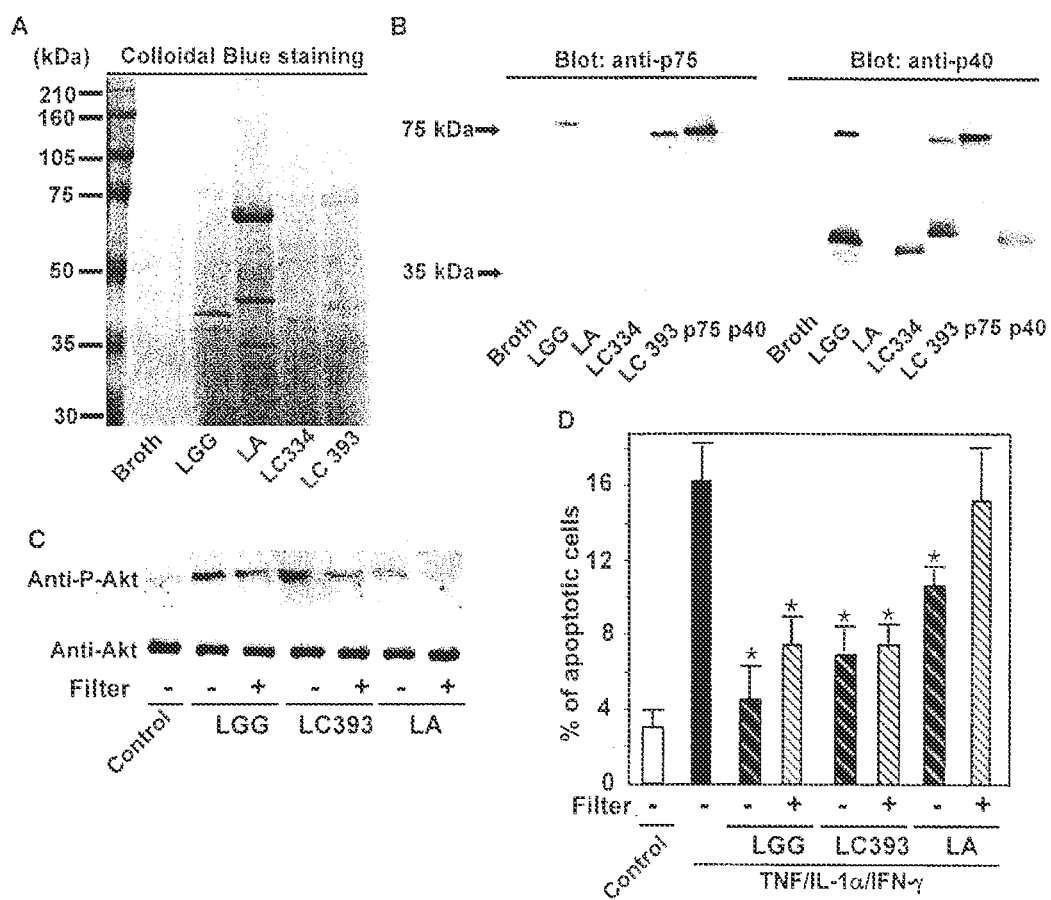
FIGS. 8A-D—Production of p75 and p40 by Lactobacilli is strain specific. Concentrated proteins recovered from indicated bacterial conditioned cell culture media using a 5 kDa cut-off filter were separated by SDS-PAGE and stained with Colloidal Blue Staining Kit (FIG. 8A), and Western blot analysis of these proteins with anti-p75 and anti-p40 antibodies was performed (FIG. 8B). To test the effects of bacteria-derived soluble factors on colon cells, the indicated bacteria were separated from YAMC cells by 0.2 µM filters during co-culture experiments for two hours. Cellular lysates were collected and Akt activation determined as in FIGS. 2A-D (FIG. 8C). To test these soluble factors' effects on preventing apoptosis, bacteria were separated in transwell co-cultures as in C, with HT29 cells for 1 hour followed by 16-hour co-treatment with "cytokine cocktail" containing TNF (100 ng/ml), IL-1α (10 ng/ml) and γ-IFN (100 ng/ml). Cells were then prepared for apoptosis assays using Annexin V-FITC staining as in FIG. 3A-D. The percentage of the early apoptotic cell populations is shown (FIG. 8D). LC334: *Lactobacillus casei* 334, LC393: *Lactobacillus casei* 393, LA: *Lactobacillus acidophilus*. *, $p<0.01$, compared with TNF/IL-1α/γ-IFN. Data in this figure represent three separate experiments.

It should be noted that when the inventors analyzed proteins present in LGG-s, they focused on p75 and p40 because they are the two major bands seen on SDS-PAGE analysis of concentrated LGG-s (FIG. 1A and FIG. 8A). LGG-s also contained a 17 kDa protein, which was recognized by anti-p40 antibody in Western blot analysis (data not shown). However, this 17 kDa protein did not bind to the ion exchange medium and therefore was not detected in chromatographically purified p75 or p40 fractions (data not shown). The investigators speculate that this 17 kDa protein may be a degradation product of p40, but does not contain the functional domain of p40 required for Akt activation.

Only a partial ORF encoding LGG p75 was characterized in this study, and therefore, it is difficult to fully compare the similarity between p75 and p40. However, two observations suggest that p75 and p40 may share some identical peptide sequences: 1) analysis of trypsin-digested peptides from p75 and p40 samples by MALDI-TOF/MS revealed several identical peaks in both preparations (data not shown), and 2) the p40 antibody recognized p75 in Western blot analysis (FIGS. 1B-C; FIG. 8B). Therefore, further studies of the C-terminal portion of p75 will be required to determine whether there is any sequence similarity between these two proteins.

Bacterial regulation of host responses through the production of biologically active products has been described in several other bacteria. Staphylococcal aureus produces lipoteichoic acid to prevent delayed-type hypersensitivity reactions through activation of the platelet-activating factor receptor (Zhang et al., 2005). In addition, Salmonella protects epithelial cells from apoptosis by sustained activation of Akt through the effector protein SopB (Knodler et al., 2005). Interestingly, low molecular weight factors secreted by LGG (<10 kDa) have been reported to stimulate Hsp25 and Hsp72 production by intestinal epithelial cells (Tao et al., 2006). However, we found LGG-s containing factors >5 kDa, but not LGG-s filtrate with factors <5 kDa, stimulate Akt activation (Yan and Polk, 2002). It is possible that multiple factors in LGG-s may regulate different epithelial cellular responses.

One long-term goal of these studies is to understand the molecular basis of p75 and p40 regulation of signaling pathways and cellular responses leading to inhibition of intestinal inflammation. Commensal bacteria inhibit inflammatory responses in part through NF-κB (Kelly et al., 2004; Neish, 2004), but the inventors have not detected any effects of LGG, p75 or p40 on NF-κB activation in intestinal epithelial cells (FIG. 2D and Yan and Polk, 2002). Because p75 and p40 activate Akt in a PI3K-dependent manner (FIG. 2B), it is important to elucidate mechanisms of signaling pathways and downstream targets determining cellular survival in intestinal epithelial cells.

In summary, this report shows that purified p75 and p40 from LGG-s protect intestinal epithelial cells from apoptosis, promote proliferation, and activate Akt in a PI3K-dependent manner in both cell and organ culture models. These soluble protein effects are further confirmed by the fact that only Lactobacillus strains that produce p75 and p40 in their supernatant show independence of direct bacterial-cell interaction for these regulatory effects. To date, p75 and p40 are the first identified probiotic bacterial soluble proteins regulating intestinal epithelial homeostasis through specific cellular signal transduction pathways. These findings support a potential application of native bacterial components to prevent cytokine-mediated gastrointestinal injury and disease.

II. PROBIOTIC SOLUBLE PROTEINS

As discussed below, the inventors have purified and characterized two soluble proteins from Lactobacillus which are designated p75 and p40. N-terminal sequences and internal peptide sequences of these proteins were determined, as described below. Multiple oligonucleotide primers were designed based on the sequences of the corresponding L. casei 334 genes and flanking DNA sequences in the L. casei genome (NCBI GeneBank accession numbers COG0791 and COG3883), and these primers were used to PCR-amplify related sequences from LGG genomic DNA.

Sequence analysis of one set of cloned PCR products revealed the presence of a 1236 bp ORF, predicted to encode a 412 amino acid protein with a calculated molecular mass of 42 kDa (FIG. 1D). The deduced full-length amino acid sequence of p40 (SEQ ID NO 1) was 79% identical to the sequence of a 396 amino acid protein of unknown function in L. casei 334 (NCBI GeneBank COG3883).

Sequence analysis of another set of cloned PCR products revealed the presence of a partial ORF that was >1488 bp in length (SEQ ID NO 3); the full-length ORF was not successfully amplified. The deduced amino acid sequence of p75 (SEQ ID NO 4) was most closely related to a 493-amino-acid cell wall-associated hydrolase of L. casei 334 (NCBI GeneBank COG0791), and exhibited 70% and 93% identity to two different regions of this L. casei 334 protein. The predicted molecular mass of the full-length cell wall-associated hydrolase of L. casei 334 (49 kDa) differs substantially from the molecular mass of the LGG p75 protein.

An analysis of the LGG p40 and p75 gene sequences and the experimentally determined N-terminal amino acid sequences of the encoded proteins indicates that both genes encode proteins with N-terminal signal sequences. The presence of signal sequences is consistent with the hypothesis that p40 and p75 are actively secreted into the culture supernatant by LGG. The p40 gene sequence and the partial p75 gene sequence do not show significant relatedness, and the experimentally determined N-terminal amino acid sequences of these two proteins are not related. Thus, based on the available sequence data, there is no evidence to suggest that p40 is a degradation product of p75. However, it is possible that there could be sequence similarity between p40 and the uncharacterized C-terminal portion of p75.

A. Purification of Proteins

Generally, "purified" will refer to a specific protein composition that has been subjected to fractionation to remove non-proteinaceous components and various other proteins, polypeptides, or peptides, and which composition substantially retains its activity, as may be assessed, for example, by the protein assays, as described herein below, or as would be known to one of ordinary skill in the art for the desired protein, polypeptide or peptide.

Where the term "substantially purified" is used, this will refer to a composition in which the specific protein, polypeptide, or peptide forms the major component of the composition, such as constituting about 50% of the proteins in the composition or more. In preferred embodiments, a substantially purified protein will constitute more than 60%, 70%, 80%, 90%, 95%, 99% or even more of the proteins in the composition.

A peptide, polypeptide or protein that is "purified to homogeneity," as applied to the present invention, means that the peptide, polypeptide or protein has a level of purity where the peptide, polypeptide or protein is substantially free from other proteins and biological components. For example, a purified peptide, polypeptide or protein will often be sufficiently free of other protein components so that degradative sequencing may be performed successfully.

Various methods for quantifying the degree of purification of proteins, polypeptides, or peptides will be known to those of skill in the art in light of the present disclosure. These include, for example, determining the specific protein activity of a fraction, or assessing the number of polypeptides within a fraction by gel electrophoresis.

To purify a desired protein, polypeptide, or peptide a natural or recombinant composition comprising at least some specific proteins, polypeptides, or peptides will be subjected to fractionation to remove various other components from the composition. In addition to those techniques described in detail herein below, various other techniques suitable for use in protein purification will be well known to those of skill in the art. These include, for example, precipitation with ammonium sulfate, PEG, antibodies and the like or by heat denaturation, followed by centrifugation; chromatography steps such as ion exchange, gel filtration, reverse phase, hydroxylapatite, lectin affinity and other affinity chromatography steps; isoelectric focusing; gel electrophoresis; and combinations of such and other techniques.

Another example is the purification of a specific fusion protein using a specific binding partner. Such purification methods are routine in the art. As the present invention provides DNA sequences for the specific proteins, any fusion protein purification method can now be practiced. This is exemplified by the generation of an specific protein-glutathione S-transferase fusion protein, expression in *E. coli*, and isolation to homogeneity using affinity chromatography on glutathione-agarose or the generation of a polyhistidine tag on the N- or C-terminus of the protein, and subsequent purification using Ni-affinity chromatography. However, given many DNA and proteins are known, or may be identified and amplified using the methods described herein, any purification method can now be employed.

Although preferred for use in certain embodiments, there is no general requirement that the protein, polypeptide, or peptide always be provided in their most purified state. Indeed, it is contemplated that less substantially purified protein, polypeptide or peptide, which are nonetheless enriched in the desired protein compositions, relative to the natural state, will have utility in certain embodiments.

Methods exhibiting a lower degree of relative purification may have advantages in total recovery of protein product, or in maintaining the activity of an expressed protein. Inactive products also have utility in certain embodiments, such as, e.g., in determining antigenicity via antibody generation.

B. Pharmaceutical Preparations

Pharmaceutical compositions of the present invention comprise an effective amount of p40 or p75 dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains p40 or p75 or additional active ingredient will be known to those of skill in the art in light of the present disclosure, as exemplified by Remington's Pharmaceutical Sciences, 18$^{th}$ Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18$^{th}$ Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The compounds of the invention may comprise different types of carriers depending on whether it is to be administered in solid, liquid or aerosol form, and whether it need to be sterile for such routes of administration as injection. The present invention can be administered orally, or rectally, but may also be administered intratracheally, intranasally, subcutaneously, mucosally, by inhalation (e.g., aerosol inhalation), by injection, by infusion or continuous infusion, topically, localized perfusion bathing target cells directly, via a catheter, via a lavage, or by other method or any combination of the foregoing as would be known to one of ordinary skill in the art (see, for example, Remington's Pharmaceutical Sciences, 18$^{th}$ Ed. Mack Printing Company, 1990, incorporated herein by reference).

The actual dosage amount of a composition of the present invention administered to a patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The compounds of the present invention may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In particular embodiments, the p40 or p75 compositions of the present invention are prepared for administration by such routes as oral ingestion. In these embodiments, the solid composition may comprise, for example, solutions, suspensions, emulsions, tablets, pills, capsules (e.g., hard or soft shelled gelatin capsules), delayed release capsules, sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain specific embodiments, an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Additional formulations which are suitable for other modes of administration include suppositories. Suppositories are solid dosage forms of various weights and shapes, usually medicated, for insertion into the rectum. After insertion, suppositories soften, melt or dissolve in the cavity. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition should be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

C. Protein Production p40 or p75 of the present invention may be produced in a native probiotic bacterium, or a recombinant cell, such as a bacterium, yeast or insect cell. The examples provided below describe the purification of p40 and p75 from native probiotic bacteria that produce these proteins as part of their normal proteome. In particular, *Lactococcus lactis* may be cultured under standard conditions, as well known to those of skill in the art.

*Lactobacillus rhamnosus* strain GG (LGG) was cultured as follows. LGG was incubated in *Lactobacillus* MRS broth at 37° C. for 24 hours, then diluted in MRS broth and incubated at 37° C. to reach log phase with density determined by OD 0.5 at A600. LGG was precipitated from MRS broth (1000×g, 15 min) and washed twice with phosphate-buffered saline (PBS) for treating cells or preparing LGG-conditioned cell culture media.

In certain embodiments, p40 or p75 may be expressed recombinantly in heterologous host cells and subsequently purified (e.g., using centrifugation and/or chromatography).

As discussed below, a variety of compositions and methods are contemplated for use in the recombinant production of these proteins.

1. Vectors

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Maniatis et al., 1989 and Ausubel et al., 1994, both incorporated herein by reference).

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described infra.

The present invention involves the use of nucleic acids encoding p40 and p75, which are set forth in SEQ ID NO:1 and SEQ ID NO:3, respectively. The sequences may be modified, given the ability of several different codons to encode a single amino acid, while still encoding for the same protein or polypeptide. Optimization of codon selection can also be undertaken in light of the particular organism used for recombinant expression. Also, fragments of the foregoing sequences may be used as probes and primers for identification, isolation, cloning and amplification of the p40 and p75 sequences as described.

a. Promoters and Enhancers

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous" or "homologous." Similarly, an enhancer may be one naturally associated with a nucleic acid sequence, located either downstream or upstream of that sequence. Alternatively, certain advantages will be gained by positioning the coding nucleic acid segment under the control of a recombinant, exogenous or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in prokaryotic recombinant DNA construction include the β-lactamase (penicillinase), lactose and tryptophan (trp) promoter systems.

Naturally, it will be important to employ a promoter and/or enhancer that effectively directs the expression of the DNA segment in the organelle, cell, tissue, organ, or organism chosen for expression. Those of skill in the art of molecular biology generally know the use of promoters, enhancers, and cell type combinations for protein expression, (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination (as per, for example, the Eukaryotic Promoter Data Base EPDB, www.epd.isb-sib.ch/) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

b. Initiation Signals

A specific initiation signal also may be required for efficient translation of coding sequences. These signals include the ATG initiation codon or adjacent sequences.

Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

c. Multiple Cloning Sites

Vectors can include a multiple cloning site (MCS), which is a nucleic acid region that contains multiple restriction enzyme sites, any of which can be used in conjunction with standard recombinant technology to digest the vector (see, for example, Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

d. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see, for example, Chandler et al., 1997, herein incorporated by reference.)

e. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

f. Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal or the bovine growth hormone polyadenylation signal, convenient and known to function well in various target cells. Polyadenylation may increase the stability of the transcript or may facilitate cytoplasmic transport.

g. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

h. Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

i. Plasmid Vectors

In certain embodiments, a plasmid vector is contemplated for use to transform a host cell. In general, plasmid vectors containing replicon and control sequences which are derived from species compatible with the host cell are used in connection with these hosts. The vector ordinarily carries a replication site, as well as marking sequences which are capable of providing phenotypic selection in transformed cells. In a non-limiting example, E. coli is often transformed using derivatives of pBR322, a plasmid derived from an E. coli species. pBR322 contains genes for ampicillin and tetracycline resistance and thus provides easy means for identifying transformed cells. The pBR plasmid, or other microbial plasmid or phage must also contain, or be modified to contain, for example, promoters which can be used by the microbial organism for expression of its own proteins.

In addition, phage vectors containing replicon and control sequences that are compatible with the host microorganism can be used as transforming vectors in connection with these hosts. For example, the phage lambda GEM™-11 may be utilized in making a recombinant phage vector which can be used to transform host cells, such as, for example, E. coli LE392.

Further useful plasmid vectors include pIN vectors (Inouye et al., 1985); and pGEX vectors, for use in generating glutathione S-transferase (GST) soluble fusion proteins for later purification and separation or cleavage. Other suitable fusion proteins are those with β-galactosidase, ubiquitin, and the like.

Bacterial host cells, for example, E. coli, comprising the expression vector, are grown in any of a number of suitable media, for example, LB. The expression of the recombinant protein in certain vectors may be induced, as would be understood by those of skill in the art, by contacting a host cell with an agent specific for certain promoters, e.g., by adding IPTG to the media or by switching incubation to a higher temperature. After culturing the bacteria for a further period, generally of 2-24 hr, the cells are collected by centrifugation and washed to remove residual media.

j. Viral Vectors

The ability of certain viruses to infect cells or enter cells via receptor-mediated endocytosis, and to integrate into host cell genome and express viral genes stably and efficiently have made them attractive candidates for the transfer of foreign nucleic acids into cells (e.g., mammalian cells). Viruses may thus be utilized that encode and express p40 or p75. Non-limiting examples of virus vectors that may be used to deliver a p40 or p75 nucleic acid are described below.

Adenoviral Vectors.

A particular method for delivery of the nucleic acid involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a tissue or cell-specific construct that has been cloned therein. Knowledge of the genetic organization or adenovirus, a 36 kb, linear, double-stranded DNA virus, allows substitution of large pieces of adenoviral DNA with foreign sequences up to 7 kb (Grunhaus and Horwitz, 1992).

AAV Vectors.

The nucleic acid may be introduced into the cell using adenovirus assisted transfection. Increased transfection efficiencies have been reported in cell systems using adenovirus coupled systems (Kelleher and Vos, 1994; Cotten et al., 1992; Curiel, 1994). Adeno-associated virus (AAV) has a high frequency of integration and it can infect non-dividing cells, thus making it useful for delivery of genes into mammalian cells, for example, in tissue culture (Muzyczka, 1992) or in vivo. AAV has a broad host range for infectivity (Tratschin et al., 1984; Laughlin et al., 1986; Lebkowski et al., 1988; McLaughlin et al., 1988). Details concerning the generation and use of rAAV vectors are described in U.S. Pat. Nos. 5,139,941 and 4,797,368, each incorporated herein by reference.

Retroviral Vectors.

Retroviruses have the ability to integrate their genes into the host genome, transferring a large amount of foreign genetic material, infecting a broad spectrum of species and cell types and of being packaged in special cell-lines (Miller, 1992). In order to construct a retroviral vector, a nucleic acid (e.g., one encoding a protein of interest) is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into a special cell line (e.g., by calcium phosphate precipitation for example), the packaging sequence allows the RNA transcript of the recombinant plasmid to be packaged into viral particles, which are then secreted into the culture media (Nicolas and Rubinstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Lentiviruses are complex retroviruses, which, in addition to the common retroviral genes gag, pol, and env, contain other genes with regulatory or structural function. Lentiviral vectors are well known in the art (see, for example, Naldini et al., 1996; Zufferey et al., 1997; Blomer et al., 1997; U.S. Pat. Nos. 6,013,516 and 5,994,136). Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif, vpr, vpu and nef are deleted making the vector biologically safe.

Recombinant lentiviral vectors are capable of infecting non-dividing cells and can be used for both in vivo and ex vivo gene transfer and expression of nucleic acid sequences. For example, recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. One may target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific.

Other Viral Vectors.

Other viral vectors may be employed as vaccine constructs in the present invention. Vectors derived from viruses such as vaccinia virus (Ridgeway, 1988; Baichwal and Sugden, 1986; Coupar et al., 1988), sindbis virus, cytomegalovirus and herpes simplex virus may be employed. They offer several attractive features for various mammalian cells (Friedmann, 1989; Ridgeway, 1988; Baichwal and Sugden, 1986; Coupar et al., 1988; Horwich et al., 1990).

Modified Viruses.

A nucleic acid to be delivered may be housed within an infective virus that has been engineered to express a specific binding ligand. The virus particle will thus bind specifically to the cognate receptors of the target cell and deliver the contents to the cell. A novel approach designed to allow specific targeting of retrovirus vectors was developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

2. Vector Delivery and Cell Transformation

Suitable methods for nucleic acid delivery for transformation of an organelle, a cell, a tissue or an organism for use with the current invention are believed to include virtually any method by which a nucleic acid (e.g., DNA) can be introduced into an organelle, a cell, a tissue or an organism, as described herein or as would be known to one of ordinary skill in the art. Such methods include, but are not limited to, direct delivery of DNA such as by ex vivo transfection (Wilson et al., 1989, Nabel et al, 1989), by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference; Tur-Kaspa et al., 1986; Potter et al., 1984); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991) and receptor-mediated transfection (Wu and Wu, 1987; Wu and Wu, 1988); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by *Agrobacterium*-mediated transformation (U.S. Pat. Nos. 5,591,616 and 5,563,055, each incorporated herein by reference); by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985), and any combination of such methods. Through the application of techniques such as these, organelle(s), cell(s), tissue(s) or organism(s) may be stably or transiently transformed.

a. Ex Vivo Transformation

Methods for transfecting vascular cells and tissues removed from an organism in an ex vivo setting are known to those of skill in the art. For example, cannine endothelial cells have been genetically altered by retrovial gene tranfer in vitro and transplanted into a canine (Wilson et al., 1989). In another example, yucatan minipig endothelial cells were tranfected by retrovirus in vitro and transplated into an artery using a double-ballonw catheter (Nabel et al., 1989). Thus, it is contemplated that cells or tissues may be removed and tranfected ex vivo using the nucleic acids of the present invention. In particular aspects, the transplanted cells or tissues may be placed into an organism. In preferred facets, a nucleic acid is expressed in the transplanted cells or tissues.

b. Injection

In certain embodiments, a nucleic acid may be delivered to an organelle, a cell, a tissue or an organism via one or more injections (i.e., a needle injection), such as, for example, subcutaneously, intradermally, intramuscularly, intervenously, intraperitoneally, etc. Methods of injection of vaccines are well known to those of ordinary skill in the art (e.g., injection of a composition comprising a saline solution). Further embodiments of the present invention include the introduction of a nucleic acid by direct microinjection. Direct microinjection has been used to introduce nucleic acid constructs into *Xenopus* oocytes (Harland and Weintraub, 1985). The amount of vector used may vary upon the nature of the antigen as well as the organelle, cell, tissue or organism used c. Electroporation

In certain embodiments of the present invention, a nucleic acid is introduced into an organelle, a cell, a tissue or an organism via electroporation. Electroporation involves the exposure of a suspension of cells and DNA to a high-voltage electric discharge. In some variants of this method, certain cell wall-degrading enzymes, such as pectin-degrading enzymes, are employed to render the target recipient cells more susceptible to transformation by electroporation than untreated cells (U.S. Pat. No. 5,384,253, incorporated herein by reference). Alternatively, recipient cells can be made more susceptible to transformation by mechanical wounding.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

To effect transformation by electroporation in cells such as, for example, plant cells, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wounding in a controlled manner. Examples of some species which have been transformed by electroporation of intact cells include maize (U.S. Pat. No. 5,384,253; Rhodes et al., 1995; D'Halluin et al., 1992), wheat (Zhou et al., 1993), tomato (Hou and Lin, 1996), soybean (Christou et al., 1987) and tobacco (Lee et al., 1989).

One also may employ protoplasts for electroporation transformation of plant cells (Bates, 1994; Lazzeri, 1995). For example, the generation of transgenic soybean plants by electroporation of cotyledon-derived protoplasts is described by Dhir and Widholm in International Patent Application No. WO 9217598, incorporated herein by reference. Other examples of species for which protoplast transformation has been described include barley (Lazzeri, 1995), sorghum (Battraw et al., 1991), maize (Bhattacharjee et al., 1997), wheat (He et al., 1994) and tomato (Tsukada, 1989).

d. Calcium Phosphate

In other embodiments of the present invention, a nucleic acid is introduced to the cells using calcium phosphate precipitation. Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

e. DEAE-Dextran

In another embodiment, a nucleic acid is delivered into a cell using DEAE-dextran followed by polyethylene glycol. In this manner, reporter plasmids were introduced into mouse myeloma and erythroleukemia cells (Gopal, 1985).

f. Sonication Loading

Additional embodiments of the present invention include the introduction of a nucleic acid by direct sonic loading. LTK$^-$ fibroblasts have been transfected with the thymidine kinase gene by sonication loading (Fechheimer et al., 1987).

g. Liposome-Mediated Transfection

In a further embodiment of the invention, a nucleic acid may be entrapped in a lipid complex such as, for example, a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is an nucleic acid complexed with Lipofectamine (Gibco BRL) or Superfect (Qiagen).

Liposome-mediated nucleic acid delivery and expression of foreign DNA in vitro has been very successful (Nicolau and Sene, 1982; Fraley et al., 1979; Nicolau et al., 1987). The feasibility of liposome-mediated delivery and expression of foreign DNA in cultured chick embryo, HeLa and hepatoma cells has also been demonstrated (Wong et al., 1980).

In certain embodiments of the invention, a liposome may be complexed with a hemagglutinating virus (HVJ). This has been shown to facilitate fusion with the cell membrane and promote cell entry of liposome-encapsulated DNA (Kaneda et al., 1989). In other embodiments, a liposome may be complexed or employed in conjunction with nuclear non-histone chromosomal proteins (HMG-1) (Kato et al., 1991). In yet further embodiments, a liposome may be complexed or employed in conjunction with both HVJ and HMG-1. In other embodiments, a delivery vehicle may comprise a ligand and a liposome.

h. Receptor Mediated Transfection

Still further, a nucleic acid may be delivered to a target cell via receptor-mediated delivery vehicles. These take advantage of the selective uptake of macromolecules by receptor-mediated endocytosis that will be occurring in a target cell. In view of the cell type-specific distribution of various receptors, this delivery method adds another degree of specificity to the present invention.

Certain receptor-mediated gene targeting vehicles comprise a cell receptor-specific ligand and a nucleic acid-binding agent. Others comprise a cell receptor-specific ligand to which the nucleic acid to be delivered has been operatively attached. Several ligands have been used for receptor-mediated gene transfer (Wu and Wu, 1987; Wagner et al., 1990; Perales et al., 1994; Myers, EPO 0273085), which establishes the operability of the technique. Specific delivery in the context of another mammalian cell type has been described (Wu and Wu, 1993; incorporated herein by reference). In certain aspects of the present invention, a ligand will be chosen to correspond to a receptor specifically expressed on the target cell population.

In other embodiments, a nucleic acid delivery vehicle component of a cell-specific nucleic acid targeting vehicle may comprise a specific binding ligand in combination with a liposome. The nucleic acid(s) to be delivered are housed within the liposome and the specific binding ligand is functionally incorporated into the liposome membrane. The liposome will thus specifically bind to the receptor(s) of a target cell and deliver the contents to a cell. Such systems have been shown to be functional using systems in which, for example, epidermal growth factor (EGF) is used in the receptor-mediated delivery of a nucleic acid to cells that exhibit upregulation of the EGF receptor.

In still further embodiments, the nucleic acid delivery vehicle component of a targeted delivery vehicle may be a liposome itself, which will preferably comprise one or more lipids or glycoproteins that direct cell-specific binding. For example, lactosyl-ceramide, a galactose-terminal asialganglioside, have been incorporated into liposomes and observed an increase in the uptake of the insulin gene by hepatocytes (Nicolau et al., 1987). It is contemplated that the tissue-specific transforming constructs of the present invention can be specifically delivered into a target cell in a similar manner.

i. Microprojectile Bombardment

Microprojectile bombardment techniques can be used to introduce a nucleic acid into at least one, organelle, cell, tissue or organism (U.S. Pat. No. 5,550,318; U.S. Pat. No. 5,538,880; U.S. Pat. No. 5,610,042; and PCT Application WO 94/09699; each of which is incorporated herein by reference). This method depends on the ability to accelerate DNA-coated microprojectiles to a high velocity allowing them to pierce cell membranes and enter cells without killing them (Klein et al., 1987). There are a wide variety of microprojectile bombardment techniques known in the art, many of which are applicable to the invention.

In this microprojectile bombardment, one or more particles may be coated with at least one nucleic acid and delivered into cells by a propelling force. Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold particles or beads. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. DNA-coated particles may increase the level of DNA delivery via particle bombardment but are not, in and of themselves, necessary.

An illustrative embodiment of a method for delivering DNA into a cell by acceleration is the Biolistics Particle Delivery System, which can be used to propel particles coated with DNA or cells through a screen, such as a stainless steel or Nytex screen, onto a filter surface covered with cells, such as for example, a monocot plant cells cultured in suspension. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

3. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny. As used herein, the terms "engineered" and "recombinant" cells or host cells are intended to refer to a cell into which an exogenous nucleic acid sequence, such as, for example, a vector, has been introduced. Therefore, recombinant cells are distinguishable from naturally occurring cells which do not contain a recombinantly introduced nucleic acid.

In certain embodiments, it is contemplated that RNAs or proteinaceous sequences may be co-expressed with other selected RNAs or proteinaceous sequences in the same host cell. Co-expression may be achieved by co-transfecting the host cell with two or more distinct recombinant vectors. Alternatively, a single recombinant vector may be constructed to include multiple distinct coding regions for RNAs, which could then be expressed in host cells transfected with the single vector.

In certain embodiments, the host cell or tissue may be comprised in at least one organism. In certain embodiments, the organism may be, but is not limited to, a prokayote (e.g., a eubacteria, an archaea) or a eukaryote (yeast), as would be understood by one of ordinary skill in the art (see, for example, webpage phylogeny.arizona.edu/tree/phylogeny.html).

Numerous cell lines and cultures are available for use as a host cell, and they can be obtained through the American Type Culture Collection (ATCC), which is an organization that serves as an archive for living cultures and genetic materials (atcc.org). An appropriate host can be determined by one of skill in the art based on the vector backbone and the desired result. A plasmid or cosmid, for example, can be introduced into a prokaryote host cell for replication of many vectors. Cell types available for vector replication and/or expressioninclude, but are not limited to, bacteria, such as E. coli (e.g., E. coli strain RR1, E. coli LE392, E. coli B, E. coli X 1776 (ATCC No. 31537) as well as E. coli W3110 (F-, lambda-, prototrophic, ATCC No. 273325), DH5α, JM109, and KC8, bacilli such as Bacillus subtilis; and other enterobacteriaceae such as Salmonella typhimurium, Serratia marcescens, various Pseudomonas specie, as well as a number of commercially available bacterial hosts such as SURE® Competent Cells and SOLOPACK™ Gold Cells (STRATAGENE®, La Jolla). In certain embodiments, bacterial cells such as E. coli LE392 are particularly contemplated as host cells for phage viruses.

Examples of eukaryotic host cells for replication and/or expression of a vector include, but are not limited to, HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

4. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986 and 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

Other examples of expression systems include STRATAGENE®'s COMPLETE CONTROL™ Inducible Mammalian Expression System, which involves a synthetic ecdysone-inducible receptor, or its pET Expression System, an E. coli expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the Pichia methanolica Expression System, which is designed for high-level production of recombinant proteins in the methylotrophic yeast Pichia methanolica. One of skill in the art would know how to express a vector, such as an expression construct, to produce a nucleic acid sequence or its cognate polypeptide, protein, or peptide.

It is contemplated that the proteins, polypeptides or peptides produced by the methods of the invention may be "overexpressed," i.e., expressed in increased levels relative to its natural expression in cells. Such overexpression may be assessed by a variety of methods, including radio-labeling and/or protein purification. However, simple and direct methods are preferred, for example, those involving SDS/PAGE and protein staining or western blotting, followed by quantitative analyses, such as densitometric scanning of the resultant gel or blot. A specific increase in the level of the recombinant protein, polypeptide or peptide in comparison to the level in natural cells is indicative of overexpression, as is a relative abundance of the specific protein, polypeptides or peptides in relation to the other proteins produced by the host cell and, e.g., visible on a gel.

In some embodiments, the expressed proteinaceous sequence forms an inclusion body in the host cell, the host cells are lysed, for example, by disruption in a cell homogenizer, washed and/or centrifuged to separate the dense inclusion bodies and cell membranes from the soluble cell components. This centrifugation can be performed under conditions whereby the dense inclusion bodies are selectively enriched by incorporation of sugars, such as sucrose, into the buffer and centrifugation at a selective speed. Inclusion bodies may be solubilized in solutions containing high concentrations of urea (e.g., 8M) or chaotropic agents such as guanidine hydrochloride in the presence of reducing agents, such as β-mercaptoethanol or DTT (dithiothreitol), and refolded into a more desirable conformation, as would be known to one of ordinary skill in the art.

D. Protein Variants

As mentioned above, modifications and/or changes may be made in the structure of p40 or p75, the present invention contemplates variation in sequence of these proteins, and the nucleic acids coding therefor, where they are nonetheless able retain substantial activity with respect to the preventative and curative aspects of the present invention.

1. Modified Polynucleotides and Polypeptides

The biological functional equivalent may comprise a polynucleotide that has been engineered to contain distinct sequences while at the same time retaining the capacity to encode the "wild-type" or standard protein. This can be accomplished to the degeneracy of the genetic code, i.e., the presence of multiple codons, which encode for the same amino acids. In one example, one of skill in the art may wish to introduce a restriction enzyme recognition sequence into a polynucleotide while not disturbing the ability of that polynucleotide to encode a protein.

In another example, a polynucleotide made be (and encode) a biological functional equivalent with more significant changes. Certain amino acids may be substituted for other amino acids in a protein structure without appreciable loss of interactive binding capacity with structures such as, for example, antigen-binding regions of antibodies, binding sites on substrate molecules, receptors, and such like. So-called "conservative" changes do not disrupt the biological activity of the protein, as the structural change is not one that impinges of the protein's ability to carry out its designed function. It is thus contemplated by the inventors that various changes may be made in the sequence of genes and proteins disclosed herein, while still fulfilling the goals of the present invention.

In terms of functional equivalents, it is well understood by the skilled artisan that, inherent in the definition of a "biologically functional equivalent" protein and/or polynucleotide, is the concept that there is a limit to the number of changes that may be made within a defined portion of the molecule while retaining a molecule with an acceptable level of equivalent biological activity. Biologically functional equivalents are thus defined herein as those proteins (and polynucleotides) in selected amino acids (or codons) may be substituted.

In general, the shorter the length of the molecule, the fewer changes that can be made within the molecule while retaining function. Longer domains may have an intermediate number of changes. The full-length protein will have the most tolerance for a larger number of changes. However, it must be appreciated that certain molecules or domains that are highly dependent upon their structure may tolerate little or no modification.

Amino acid substitutions are generally based on the relative similarity of the amino acid side-chain substituents, for example, their hydrophobicity, hydrophilicity, charge, size, and/or the like. An analysis of the size, shape and/or type of the amino acid side-chain substituents reveals that arginine, lysine and/or histidine are all positively charged residues; that alanine, glycine and/or serine are all a similar size; and/or that phenylalanine, tryptophan and/or tyrosine all have a generally similar shape. Therefore, based upon these considerations, arginine, lysine and/or histidine; alanine, glycine and/or serine; and/or phenylalanine, tryptophan and/or tyrosine; are defined herein as biologically functional equivalents.

To effect more quantitative changes, the hydropathic index of amino acids may be considered. Each amino acid has been assigned a hydropathic index on the basis of their hydrophobicity and/or charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and/or arginine (−4.5).

The importance of the hydropathic amino acid index in conferring interactive biological function on a protein is generally understood in the art (Kyte & Doolittle, 1982, incorporated herein by reference). It is known that certain amino acids may be substituted for other amino acids having a similar hydropathic index and/or score and/or still retain a similar biological activity. In making changes based upon the hydropathic index, the substitution of amino acids whose hydropathic indices are within ±2 is preferred, those which are within ±1 are particularly preferred, and/or those within ±0.5 are even more particularly preferred.

It also is understood in the art that the substitution of like amino acids can be made effectively on the basis of hydrophilicity, particularly where the biological functional equivalent protein and/or peptide thereby created is intended for use in immunological embodiments, as in certain embodiments of the present invention. U.S. Pat. No. 4,554,101, incorporated herein by reference, states that the greatest local average hydrophilicity of a protein, as governed by the hydrophilicity of its adjacent amino acids, correlates with its immunogenicity and/or antigenicity, i.e., with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In making changes based upon similar hydrophilicity values, the substitution of amino acids whose hydrophilicity values are within ±2 is preferred, those which are within ±1 are particularly preferred, and/or those within ±0.5 are even more particularly preferred.

2. Altered Amino Acids

The present invention, in many aspects, relies on the synthesis of peptides and polypeptides in cyto, via transcription and translation of appropriate polynucleotides. These peptides and polypeptides will include the twenty "natural" amino acids, and post-translational modifications thereof. However, in vitro peptide synthesis permits the use of modified and/or unusual amino acids. A table of exemplary, but not limiting, modified and/or unusual amino acids is provided herein below.

TABLE 1

Modified and/or Unusual Amino Acids

| Abbr. | Amino Acid | Abbr. | Amino Acid |
| --- | --- | --- | --- |
| Aad | 2-Aminoadipic acid | EtAsn | N-Ethylasparagine |
| BAad | 3-Aminoadipic acid | Hyl | Hydroxylysine |
| BAla | beta-alanine, beta-Aminopropionic acid | AHyl | allo-Hydroxylysine |
| Abu | 2-Aminobutyric acid | 3Hyp | 3-Hydroxyproline |
| 4Abu | 4-Aminobutyric acid, piperidinic acid | 4Hyp | 4-Hydroxyproline |
| Acp | 6-Aminocaproic acid | Ide | Isodesmosine |
| Ahe | 2-Aminoheptanoic acid | Aile | allo-Isoleucine |
| Aib | 2-Aminoisobutyric acid | MeGly | N-Methylglycine, sarcosine |
| BAib | 3-Aminoisobutyric acid | MeIle | N-Methylisoleucine |
| Apm | 2-Aminopimelic acid | MeLys | 6-N-Methyllysine |
| Dbu | 2,4-Diaminobutyric acid | MeVal | N-Methylvaline |
| Des | Desmosine | Nva | Norvaline |
| Dpm | 2,2'-Diaminopimelic acid | Nle | Norleucine |
| Dpr | 2,3-Diaminopropionic acid | Orn | Ornithine |
| EtGly | N-Ethylglycine | | |

3. Mimetics

In addition to the biological functional equivalents discussed above, the present inventors also contemplate that structurally similar compounds may be formulated to mimic the key portions of peptide or polypeptides of the present invention. Such compounds, which may be termed peptidomimetics, may be used in the same manner as the peptides of the invention and, hence, also are functional equivalents.

Certain mimetics that mimic elements of protein secondary and tertiary structure are described in Johnson et al. (1993). The underlying rationale behind the use of peptide mimetics is that the peptide backbone of proteins exists chiefly to orient amino acid side chains in such a way as to facilitate molecular interactions, such as those of antibody and/or antigen. A peptide mimetic is thus designed to permit molecular interactions similar to the natural molecule.

Some successful applications of the peptide mimetic concept have focused on mimetics of β-turns within proteins, which are known to be highly antigenic. Likely β-turn structure within a polypeptide can be predicted by computer-based algorithms, as discussed herein. Once the component amino acids of the turn are determined, mimetics can be constructed to achieve a similar spatial orientation of the essential elements of the amino acid side chains.

Other approaches have focused on the use of small, multidisulfide-containing proteins as attractive structural templates for producing biologically active conformations that mimic the binding sites of large proteins (Vita et al., 1998). A structural motif that appears to be evolutionarily conserved in certain toxins is small (30-40 amino acids), stable, and high permissive for mutation. This motif is composed of a beta sheet and an alpha helix bridged in the interior core by three disulfides.

Beta II turns have been mimicked successfully using cyclic L-pentapeptides and those with D-amino acids (Weisshoff et al., 1999). Also, Johannesson et al. (1999) report on bicyclic tripeptides with reverse turn inducing properties.

Methods for generating specific structures have been disclosed in the art. For example, alpha-helix mimetics are disclosed in U.S. Pat. Nos. 5,446,128, 5,710,245, 5,840,833 and 5,859,184. Theses structures render the peptide or protein more thermally stable, also increase resistance to proteolytic degradation. Six, seven, eleven, twelve, thirteen and fourteen membered ring structures are disclosed.

Methods for generating conformationally restricted beta turns and beta bulges are described, for example, in U.S. Pat. Nos. 5,440,013, 5,618,914 and 5,670,155. Beta-turns permit changed side substituents without having changes in corresponding backbone conformation, and have appropriate termini for incorporation into peptides by standard synthesis procedures. Other types of mimetic turns include reverse and gamma turns. Reverse turn mimetics are disclosed in U.S. Pat. Nos. 5,475,085 and 5,929,237, and gamma turn mimetics are described in U.S. Pat. Nos. 5,672,681 and 5,674,976.

III. EPITHELIAL CELL DISORDER (ECD)

A p40 or p75 composition of the present invention may be used to treat an an disorder that involves pathologic apoptosis of epithelial cells, in particular that caused by cytokines. In certain embodiments, the ECD treated by the present invention may be an inflammatory bowel disease such as ulcerative colitis or Crohn's disease. However, the term "inflammatory bowel disease" or "IBD", as used herein, describes a broad class of diseases characterized by inflammation of at least part of the gastrointestinal tract. IBD symptoms may include inflammation of the intestine and resulting in abdominal cramping and persistent diarrhea. Inflammatory bowel diseases include ulcerative colitis (UC), Crohn's disease (CD), indeterminate colitis, chronic colitis, discontinuous or patchy disease, ileal inflammation, extra-colonic inflammation, granulomatous inflammation in response to ruptured crypts, aphthous ulcers, transmural inflammation, microscopic colitis, diverticulitis and diversion colitis. It may also include gastrointestinal infections, such as those caused by cholera, rotavirus or enterotoxigenic *E. coli*.

A. Ulcerative Colitis

Ulcerative colitis is a disease that causes inflammation and sores, called ulcers, in the lining of the large intestine. The inflammation usually occurs in the rectum and lower part of the colon, but it may affect the entire colon. Ulcerative colitis rarely affects the small intestine except for the end section, called the terminal ileum. Ulcerative colitis may also be called colitis or proctitis. The inflammation makes the colon empty frequently, causing diarrhea. Ulcers form in places where the inflammation has killed the cells lining the colon; the ulcers bleed and produce pus.

Ulcerative colitis may occur in people of any age, but most often it starts between ages 15 and 30, or less frequently between ages 50 and 70. Children and adolescents sometimes develop the disease. Ulcerative colitis affects men and women equally and appears to run in some families. Theories about what causes ulcerative colitis abound, but none have been proven. The most popular theory is that the body's immune system reacts to a virus or a bacterium by causing ongoing inflammation in the intestinal wall. People with ulcerative colitis have abnormalities of the immune system, but doctors do not know whether these abnormalities are a cause or a result of the disease. Ulcerative colitis is not caused by emotional distress or sensitivity to certain foods or food products, but these factors may trigger symptoms in some people.

The most common symptoms of ulcerative colitis are abdominal pain and bloody diarrhea. Patients also may experience fatigue, weight loss, loss of appetite, rectal bleeding, and loss of body fluids and nutrients. About half of patients have mild symptoms. Others suffer frequent fever, bloody diarrhea, nausea, and severe abdominal cramps. Ulcerative colitis may also cause problems such as arthritis, inflammation of the eye, liver disease (hepatitis, cirrhosis, and primary sclerosing cholangitis), osteoporosis, skin rashes, and anemia. No one knows for sure why problems occur outside the colon. Scientists think these complications may occur when the immune system triggers inflammation in other parts of the body. Some of these problems go away when the colitis is treated.

A thorough physical exam and a series of tests may be required to diagnose ulcerative colitis. Blood tests may be done to check for anemia, which could indicate bleeding in the colon or rectum. Blood tests may also uncover a high white blood cell count, which is a sign of inflammation somewhere in the body. By testing a stool sample, the doctor can detect bleeding or infection in the colon or rectum. The doctor may do a colonoscopy or sigmoidoscopy. For either test, the doctor inserts an endoscope—a long, flexible, lighted tube connected to a computer and TV monitor—into the anus to see the inside of the colon and rectum. The doctor will be able to see any inflammation, bleeding, or ulcers on the colon wall. During the exam, the doctor may do a biopsy, which involves taking a sample of tissue from the lining of the colon to view with a microscope. A barium enema x ray of the colon may also be required. This procedure involves filling the colon with barium, a chalky white solution. The barium shows up white on x-ray film, allowing the doctor a clear view of the colon, including any ulcers or other abnormalities that might be there.

Treatment for ulcerative colitis depends on the seriousness of the disease. Most people are treated with medication. In severe cases, a patient may need surgery to remove the diseased colon. Surgery is the only cure for ulcerative colitis. Some people whose symptoms are triggered by certain foods are able to control the symptoms by avoiding foods that upset their intestines, like highly seasoned foods, raw fruits and vegetables, or milk sugar (lactose). Each person may experience ulcerative colitis differently, so treatment is adjusted for each individual. Emotional and psychological support is important. Some people have remissions—periods when the symptoms go away—that last for months or even years. However, most patients' symptoms eventually return. This changing pattern of the disease means one cannot always tell when a treatment has helped. Some people with ulcerative colitis may need medical care for some time, with regular doctor visits to monitor the condition.

The goal of therapy is to induce and maintain remission, and to improve the quality of life for people with ulcerative colitis. Several types of drugs are available:

Aminosalicylates—drugs that contain 5-aminosalicyclic acid (5-ASA), help control inflammation. Sulfasalazine is a combination of sulfapyridine and 5-ASA and is used to induce and maintain remission. The sulfapyridine component carries the anti-inflammatory 5-ASA to the intestine. However, sulfapyridine may lead to side effects such as include nausea, vomiting, heartburn, diarrhea, and headache. Other 5-ASA agents such as olsalazine, mesalamine, and balsalazide, have a different carrier, offer fewer side effects, and may be used by people who cannot take sulfasalazine. 5-ASAs are given orally, through an enema, or in a suppository, depending on the location of the inflammation in the colon. Most people with mild or moderate ulcerative colitis are treated with this group of drugs first.

Corticosteroids—such as prednisone and hydrocortisone also reduce inflammation. They may be used by people who have moderate to severe ulcerative colitis or who do not respond to 5-ASA drugs. Corticosteroids, also known as steroids, can be given orally, intravenously, through an enema, or in a suppository, depending on the location of the inflammation. These drugs can cause side effects such as weight gain, acne, facial hair, hypertension, mood swings, and an increased risk of infection. For this reason, they are not recommended for long-term use.

Immunomodulators—such as azathioprine and 6-mercapto-purine (6-MP) reduce inflammation by affecting the immune system. They are used for patients who have not responded to 5-ASAs or corticosteroids or who are dependent on corticosteroids. However, immunomodulators are slow-acting and may take up to 6 months before the full benefit is seen. Patients taking these drugs are monitored for complications including pancreatitis and hepatitis, a reduced white blood cell count, and an increased risk of infection. Cyclosporine A may be used with 6-MP or azathioprine to treat active, severe ulcerative colitis in people who do not respond to intravenous corticosteroids.

Other drugs may be given to relax the patient or to relieve pain, diarrhea, or infection.

Occasionally, symptoms are severe enough that the person must be hospitalized. For example, a person may have severe bleeding or severe diarrhea that causes dehydration. In such cases the doctor will try to stop diarrhea and loss of blood, fluids, and mineral salts. The patient may need a special diet, feeding through a vein, medications, or sometimes surgery.

About 25-40% of ulcerative colitis patients must eventually have their colons removed because of massive bleeding, severe illness, rupture of the colon, or risk of cancer. Sometimes the doctor will recommend removing the colon if medical treatment fails or if the side effects of corticosteroids or other drugs threaten the patient's health. Surgery to remove the colon and rectum, known as proctocolectomy, is followed by one of the following:

Ileostomy, in which the surgeon creates a small opening in the abdomen, called a stoma, and attaches the end of the small intestine, called the ileum, to it. Waste will travel through the small intestine and exit the body through the stoma. The stoma is about the size of a quarter and is usually located in the lower right part of the abdomen near the beltline. A pouch is worn over the opening to collect waste, and the patient empties the pouch as needed.

Ileoanal anastomosis, or pull-through operation, which allows the patient to have normal bowel movements because it preserves part of the anus. In this operation, the surgeon removes the diseased part of the colon and the inside of the rectum, leaving the outer muscles of the rectum. The surgeon then attaches the ileum to the inside of the rectum and the anus, creating a pouch. Waste is stored in the pouch and passed through the anus in the usual manner. Bowel movements may be more frequent and watery than before the procedure. Inflammation of the pouch (pouchitis) is a possible complication.

Not every operation is appropriate for every person. Which surgery to have depends on the severity of the disease and the patient's needs, expectations, and lifestyle. People faced with this decision should get as much information as possible by talking to their doctors, to nurses who work with colon surgery patients (enterostomal therapists), and to other colon surgery patients. Patient advocacy organizations can direct people to support groups and other information resources.

Most people with ulcerative colitis will never need to have surgery. If surgery does become necessary, however, some people find comfort in knowing that after the surgery, the colitis is cured and most people go on to live normal, active lives.

B. Crohn's Disease

Crohn's disease is characterized by intestinal inflammation and the development of intestinal stenosis and fistulas; neuropathy often accompanies these symptoms. One hypothesis for the etiology of Crohn's disease is that a failure of the intestinal mucosal barrier, possibly resulting from genetic susceptibilities and environmental factors (e.g., smoking), exposes the immune system to antigens from the intestinal lumen including bacterial and food antigens (e.g., Soderholm et al., 1999; Hollander et al., 1986; Hollander, 1992). Another hypothesis is that persistent intestinal infection by pathogens such as *Mycobacterium paratuberculosis*, *Listeria monocytogenes*, abnormal *Escherichia coli*, or paramyxovirus, stimulates the immune response; or alternatively, symptoms result from a dysregulated immune response to ubiquitous antigens, such as normal intestinal microflora and the metabolites and toxins they produce (Sartor, 1997). The presence of IgA and IgG anti-*Sacccharomyces cerevisiae* antibodies (ASCA) in the serum was found to be highly diagnostic of pediatric Crohn's disease (Ruemmele et al., 1998; Hoffenberg et al., 1999).

Recent efforts to develop diagnostic and treatment tools against Crohn's disease have focused on the central role of cytokines (Schreiber, 1998; van Hogezand & Verspaget, 1998). Cytokines are small secreted proteins or factors (5 to 20 kD) that have specific effects on cell-to-cell interactions, intercellular communication, or the behavior of other cells. Cytokines are produced by lymphocytes, especially $T_H1$ and $T_H2$ lymphocytes, monocytes, intestinal macrophages, granulocytes, epithelial cells, and fibroblasts (reviewed in Rogler &. Andus, 1998; Galley & Webster, 1996). Some cytokines are pro-inflammatory (e.g., TNF-$\alpha$, IL-1($\alpha$ and $\beta$), IL-6, IL-8, IL-12, or leukemia inhibitory factor (LIF)); others are anti-inflammatory (e.g., IL-1 receptor antagonist, IL-4, IL-10, IL-11, and TGF-$\beta$). However, there may be overlap and functional redundancy in their effects under certain inflammatory conditions.

In active cases of Crohn's disease, elevated concentrations of TNF-$\alpha$ and IL-6 are secreted into the blood circulation, and TNF-$\alpha$, IL-1, IL-6, and IL-8 are produced in excess locally by mucosal cells (id.; Funakoshi et al., 1998). These cytokines can have far-ranging effects on physiological systems including bone development, hematopoiesis, and liver, thyroid, and neuropsychiatric function. Also, an imbalance of the IL-1$\beta$/IL-1ra ratio, in favor of pro-inflammatory IL-1$\beta$, has been observed in patients with Crohn's disease (Rogler & Andus, 1998; Saiki et al., 1998; Dionne et al., 1998; but see Kuboyama, 1998). One study suggested that cytokine profiles in stool samples could be a useful diagnostic tool for Crohn's disease (Saiki et al., 1998).

Anti-inflammatory drugs, such as 5-aminosalicylates (e.g., mesalamine) or corticosteroids, are typically prescribed, but are not always effective (reviewed in Botoman et al., 1998). Immunosuppression with cyclosporine is sometimes beneficial for patients resistant to or intolerant of corticosteroids (Brynskov et al., 1989). In Crohn's disease, a dysregulated immune response is skewed toward cell-mediated immunopathology (Murch, 1998). But immunosuppressive drugs, such as cyclosporine, tacrolimus, and mesalamine have been used to treat corticosteroid-resistant cases of Crohn's disease with mixed success (Brynskov et al., 1989; Fellerman et al., 1998). Nevertheless, surgical correction is eventually required in 90% of patients; 50% undergo colonic resection (Leiper et al., 1998; Makowiec et al., 1998). The recurrence rate after surgery is high, with 50% requiring further surgery within 5 years (Leiper et al., 1998; Besnard et al., 1998). Other therapies include the use of various cytokine antagonists (e.g., IL-1ra), inhibitors (e.g., of IL-1$\beta$ converting enzyme and antioxidants) and anti-cytokine antibodies (Rogler and Andus, 1998; van Hogezand & Verspaget, 1998; Reimund et al., 1998; Lugering et al., 1998; McAlindon et al., 1998). Monoclonal antibodies against TNF-$\alpha$ have been tried with some success in the treatment of Crohn's disease (Targan et al., 1997; Stack et al., 1997; van Dullemen et al., 1995).

Another approach to the treatment of Crohn's disease has focused on at least partially eradicating the bacterial community that may be triggering the inflammatory response and replacing it with a non-pathogenic community. For example, U.S. Pat. No. 5,599,795 discloses a method for the prevention and treatment of Crohn's disease in human patients. Their method was directed to sterilizing the intestinal tract with at least one antibiotic and at least one anti-fungal agent to kill off the existing flora and replacing them with different, select, well-characterized bacteria taken from normal humans. Borody taught a method of treating Crohn's disease by at least partial removal of the existing intestinal microflora by lavage and replacement with a new bacterial community introduced by fecal inoculum from a disease-screened human donor or by a composition comprising *Bacteroides* and *Escherichia coli* species. (U.S. Pat. No. 5,443,826). However, there has been no known cause of Crohn's disease to which diagnosis and/or treatment could be directed.

C. Irritable Bowel Syndrome

Irritable bowel syndrome, or IBS, is a problem that affects mainly the bowel or large intestine. The word syndrome implies a group of symptoms, and IBS is a syndrome because it can cause several symptoms. For example, IBS causes cramping, bloating, gas, diarrhea, and constipation. IBS is not a disease. It's a functional disorder, which means that the bowel doesn't work as it should.

With IBS, the nerves and muscles in the bowel are extra-sensitive. For example, the muscles may contract too after eating. These contractions can cause cramping and diarrhea during or shortly after a meal. Or the nerves can be overly sensitive to the stretching of the bowel (because of gas, for example). Cramping or pain can result. Emotional stress will not cause a person to develop IBS. But if you already have IBS, stress can trigger symptoms. In fact, the bowel can overreact to all sorts of things, including food, exercise, and hormones. Foods that tend to cause symptoms include milk products, chocolate, alcohol, caffeine, carbonated drinks, and fatty foods. In some cases, simply eating a large meal will trigger symptoms. Women with IBS often have more symptoms during their menstrual periods.

The main symptoms of IBS are crampy pain in the stomach area (abdomen), painful diarrhea or constipation, mucus in the stool, swollen or bloated abdomen, and the feeling that you have not finished a bowel movement. IBS has no cure, but you can do things to relieve symptoms. Treatment may involve diet changes, medicine and stress relief. A combination of things to may work best.

Some foods that may cause symptoms are fatty foods like french fries, milk products like cheese or ice cream, chocolate, alcohol, caffeine and carbonated drinks like soda. By contrast, some foods will help IBS. Fiber reduces IBS symptoms—especially constipation—because it makes stool soft, bulky, and easier to pass. Fiber is found in bran, bread, cereal, beans, fruit, and vegetables. Adding foods with fiber to the diet should be done gradually, allowing the body to get used to them. Too much fiber all at once might cause gas, which can trigger symptoms in a person with IBS. Besides telling more foods with fiber, the doctor might also prescribe a fiber pill or drinking water mixed with a special high-fiber powder.

Large meals can cause cramping and diarrhea in people with IBS. If this happens, four or five smaller meals per day is recommended, or simply eating less at each meal. If necessary, the doctor may prescribe medicine to help with symptoms, such as laxatives to treat constipation, antispasmodics to slow contractions in the bowel, which helps with diarrhea and pain, and antidepressants to help those who have severe pain.

D. Necrotizing Enterocolitis

Necrotizing enterocolitis is an acquired disease, primarily in premature infants or sick newborns, in which intestinal tissue dies. In necrotizing enterocolitis, the lining of the intestinal wall dies and the tissue sloughs off. The cause for this disorder is unknown, but it is thought that a decreased blood flow to the bowel keeps the bowel from producing the normal protective mucus. Bacteria in the intestine may also be a cause. At risk are small, premature infants, infants who are fed concentrated formulas, infants in a nursery where an outbreak has occured (suggesting an infectious cause), and infants who have received blood exchange transfusions.

Necrotizing enterocolitis is a serious disease with a death rate approaching 25%. The outcome is improved by aggressive, early treatment.

Symptoms include abdominal distention, vomiting, feeding intolerance, blood in the stool, lethargy, temperature instability, and diarrhea. Diagnosis usually involves abdominal x-ray, and examation for occult stool blood, elevated white count, thrombocytopenia, and lactic acidosis. In an infant suspected of having necrotizing enterocolitis, feedings are stopped and gas is relieved from the bowel by inserting a small tube into the stomach. IV fluid replaces formula or breast milk. Antibiotic therapy is started. The infant's condition is monitored with abdominal x-rays, blood tests, and blood gases. If intestinal perforation (hole) or peritonitis (inflammation of the abdominal wall) develops, surgery is indicated. The dead bowel tissue is removed and a colostomy or ileostomy is performed. The bowel is then reconnected several weeks or months later when the infection and inflammation have healed.

E. Celiac Disease

Celiac disease is a digestive disease that damages the small intestine and interferes with absorption of nutrients from food. People who have celiac disease cannot tolerate gluten, a protein found in wheat, rye, and barley. Gluten is found mainly in foods, but is also found in everyday products such as stamp and envelope adhesive, medicines, and vitamins. When people with celiac disease eat foods or use products containing gluten, their immune system responds by damaging the small intestine. The tiny, finger-like protrusions lining the small intestine are damaged or destroyed. Called villi, they normally allow nutrients from food to be absorbed into the bloodstream. Without healthy villi, a person becomes malnourished, regardless of the quantity of food eaten.

Because the body's own immune system causes the damage, celiac disease is considered an autoimmune disorder. However, it is also classified as a disease of malabsorption because nutrients are not absorbed. Celiac disease is also known as celiac sprue, nontropical sprue, and gluten-sensitive enteropathy. Celiac disease is a genetic disease, meaning it runs in families. Sometimes the disease is triggered—or becomes active for the first time—after surgery, pregnancy, childbirth, viral infection, or severe emotional stress.

Data on the prevalence of celiac disease is spotty. In Italy, about 1 in 250 people and in Ireland about 1 in 300 people have celiac disease. Recent studies have shown that it may be more common in Africa, South America, and Asia than previously believed. Until recently, celiac disease was thought to be uncommon in the United States. However, studies have shown that celiac disease is very common. Recent findings estimate about 2 million people in the United States have celiac disease, or about 1 in 133 people. Among people who have a first-degree relative diagnosed with celiac disease, as many as 1 in 22 people may have the disease. Celiac disease could be under diagnosed in the United States for a number of reasons including (i) celiac symptoms can be attributed to other problems; (ii) many doctors are not knowledgeable about the disease; and (iii) only a small number of U.S. laboratories are experienced and skilled in testing for celiac disease. More research is needed to learn the true prevalence of celiac disease among Americans.

Celiac disease affects people differently. Symptoms may occur in the digestive system, or in other parts of the body. For example, one person might have diarrhea and abdominal pain, while another person may be irritable or depressed. In fact, irritability is one of the most common symptoms in children. Symptoms of celiac disease may include one or more of the following: gas, recurring abdominal bloating and pain, chronic diarrhea, pale, foul-smelling or fatty stool, weight loss/gain, fatigue, unexplained anemia, bone or joint pain, osteoporosis, osteopenia, behavioral changes, tingling numbness in the legs (from nerve damage), muscle cramps, seizures, missed menstrual periods (often because of excessive weight loss), infertility, recurrent miscarriage, delayed growth, failure to thrive in infants, pale sores inside the mouth (called aphthous ulcers), tooth discoloration or loss of enamel, and itchy skin rash (dermatitis herpetiformis).

A person with celiac disease may have no symptoms. People without symptoms are still at risk for the complications of celiac disease, including malnutrition. The longer a person goes undiagnosed and untreated, the greater the chance of developing malnutrition and other complications. Anemia, delayed growth, and weight loss are signs of malnutrition: The body is just not getting enough nutrients. Malnutrition is a serious problem for children because they need adequate nutrition to develop properly.

The length of time a person is breastfed, the age a person started eating gluten-containing foods, and the amount of gluten containing foods one eats are three factors thought to play a role in when and how celiac appears. Some studies have shown, for example, that the longer a person was breastfed, the later the symptoms of celiac disease appear and the more uncommon the symptoms.

Recognizing celiac disease can be difficult because some of its symptoms are similar to those of other diseases. In fact, sometimes celiac disease is confused with irritable bowel syndrome, iron-deficiency anemia caused by menstrual blood loss, Crohn's disease, diverticulitis, intestinal infections, and chronic fatigue syndrome. As a result, celiac disease is commonly under diagnosed or misdiagnosed.

Recently, researchers discovered that people with celiac disease have higher than normal levels of certain autoantibodies in their blood. Antibodies are protective proteins produced by the immune system in response to substances that the body perceives to be threatening. Autoantibodies are proteins that react against the body's own molecules or tissues. To diagnose celiac disease, physicians will usually test blood to measure levels of Immunoglobulin A (IgA), anti-tissue transglutaminase (tTGA) and IgA anti-endomysium antibodies (AEA). Before being tested, one should continue to eat a regular diet that includes foods with gluten, such as breads and pastas. If a person stops eating foods with gluten before being tested, the results may be negative for celiac disease even if celiac disease is actually present.

If the tests and symptoms suggest celiac disease, the doctor will perform a small bowel biopsy. During the biopsy, the doctor removes a tiny piece of tissue from the small intestine to check for damage to the villi. To obtain the tissue sample, the doctor eases an endoscope through the mouth and stomach into the small intestine. Using instruments passed through the endoscope, the doctor then takes the sample.

Screening for celiac disease involves testing for the presence of antibodies in the blood in people without symptoms. Americans are not routinely screened for celiac disease. Testing for celiac-related antibodies in children less than 5 years old may not be reliable. However, since celiac disease is hereditary, family members, particularly first-degree relatives—meaning parents, siblings, or children of people who have been diagnosed—may wish to be tested for the disease. About 5 to 15 percent of an affected person's first-degree relatives will also have the disease. About 3 to 8 percent of people with type 1 diabetes will have biopsy-confirmed celiac disease and 5 to 10 percent of people with Down syndrome will be diagnosed with celiac disease.

The only treatment for celiac disease is to follow a gluten-free diet. When a person is first diagnosed with celiac disease, the doctor usually will ask the person to work with a dietitian on a gluten-free diet plan. A dietitian is a health care professional who specializes in food and nutrition. Someone with celiac disease can learn from a dietitian how to read ingredient lists and identify foods that contain gluten in order to make informed decisions at the grocery store and when eating out. For most people, following this diet will stop symptoms, heal existing intestinal damage, and prevent further damage. Improvements begin within days of starting the diet. The small intestine is usually completely healed in 3 to 6 months in children and younger adults and within 2 years for older adults. Healed means a person now has villi that can absorb nutrients from food into the bloodstream.

In order to stay well, people with celiac disease must avoid gluten for the rest of their lives. Eating any gluten, no matter how small an amount, can damage the small intestine. The damage will occur in anyone with the disease, including people without noticeable symptoms. Depending on a person's age at diagnosis, some problems will not improve, such as delayed growth and tooth discoloration.

Some people with celiac disease show no improvement on the gluten-free diet. The condition is called unresponsive celiac disease. The most common reason for poor response is that small amounts of gluten are still present in the diet. Advice from a dietitian who is skilled in educating patients about the gluten-free diet is essential to achieve best results.

Rarely, the intestinal injury will continue despite a strictly gluten-free diet. People in this situation have severely damaged intestines that cannot heal. Because their intestines are not absorbing enough nutrients, they may need to directly receive nutrients into their bloodstream through a vein (intravenously). People with this condition may need to be evaluated for complications of the disease. Researchers are now evaluating drug treatments for unresponsive celiac disease.

A gluten-free diet means not eating foods that contain wheat (including spelt, triticale, and kamut), rye, and barley. The foods and products made from these grains are also not allowed. In other words, a person with celiac disease should not eat most grain, pasta, cereal, and many processed foods. Despite these restrictions, people with celiac disease can eat a well balanced diet with a variety of foods, including gluten-free bread and pasta. For example, people with celiac disease can use potato, rice, soy, amaranth, quinoa, buckwheat, or bean flour instead of wheat flour. They can buy gluten-free bread, pasta, and other products from stores that carry organic foods, or order products from special food companies. Gluten-free products are increasingly available from regular stores. Gluten is also used in some medications. One should check with the pharmacist to learn whether medications used contain gluten. Since gluten is also sometimes used as an additive in unexpected products, it is important to read all labels. If the ingredients are not listed on the product label, the manufacturer of the product should provide the list upon request. With practice, screening for gluten becomes second nature.

Damage to the small intestine and the resulting nutrient absorption problems put a person with celiac disease at risk for malnutrition and anemia as well as several diseases and health problems. Lymphoma and adenocarcinoma are cancers that can develop in the intestine. Osteoporosis is a condition in which the bones become weak, brittle, and prone to breaking Poor calcium absorption contributes to osteoporosis. Miscarriage and congenital malformation of the baby, such as neural tube defects, are risks for pregnant women with untreated celiac disease because of nutrient absorption problems. Short stature refers to being significantly under-the-average height. Short stature results when childhood celiac disease prevents nutrient absorption during the years when nutrition is critical to a child's normal growth and development. Children who are diagnosed and treated before their growth stops may have a catch-up period. People with celiac disease also tend to have other autoimmune diseases. The connection between celiac disease and these diseases may be genetic. These diseases include thyroid disease, systemic lupus erythematosus, type 1 diabetes, liver disease, collagen vascular disease, rheumatoid arthritis and Sjögren's syndrome.

F. HIV Enteropathy

HIV enteropathy is a syndrome characterized by chronic, well-established diarrhea (greater than one month in duration) without an identified infectious cause after thorough evaluation, in an HIV-positive individual. It is thought to be due to direct or indirect effects of HIV on the enteric mucosa. HIV enteropathy is a diagnosis of exclusion and can be made only after other forms of diarrheal illness have been ruled out. It presents with a pathology similar to that of celiac disease, and gluten-free diets have been suggested to deal with the disorder.

G. *Helicobacter* Gastritis

*Heliobacter pylori* can cause infections of the stomach that may contribute to the development of dyspepsia (heartburn, bloating and nausea), gastritis (inflammation of the stomach), and ulcers in the stomach and duodenum. *H. pylori* is a fragile bacteria that has found an ideal home in the protective mucous layer of the stomach. These bacteria have long threads protruding from them that attach to the underlying stomach cells. The mucous layer that protects the stomach cells from acid also protects *H. pylori*. These bacteria do not actually invade the stomach cells as certain other bacteria can. The infection, however, is very real and it does cause the body to react. Infection-fighting white blood cells move into the area, and the body develops *H. pylori* antibodies in the blood.

*H. pylori* infection likely occurs when an individual swallows the bacteria in food or on contaminated utensils. The infection is likely one of the most common in the world, it increases with age, and also is found young people in the developing countries. In many cases it does not produce symptoms, and even if symptomatic, the infection remains localized to the gastric area, and persists unless specific treatment is given. *H. pylori* infection can be diagnosed by endoscopic biopsy followed by testing of the removed tissue for the bacteria, a breath test, or a blood test (measuring antibodies against these bacteria present in the blood).

Symptoms include discomfort, bloating, nausea and perhaps vomiting, as well as ulcers. The symptoms may be relieved by antacids, milk, or other medications that reduce stomach acidity. With stomach ulcers, *H. pylori* infection is found in 60 to 80 percent of the cases. Over 90% of all patients who develop duodenal ulcers also have *H. pylori* infection in the stomach as well. Physicians now accept the fact that the infection is directly related to the development of duodenal ulcers. It is fairly easy to clear duodenal ulcers with strong acid-reducing medicines, but the ulcers will recur unless the *H. pylori* infection is also cleared. In addition, two types of cancer are known to be related to *H. pylori* infection—stomach cancer and lymphoma.

If there are no symptoms, a doctor made decide no treatment need be given. Increasingly, physicians are treating the acute ulcers with acid-reducing medicines while also treating *H. pylori* infection with antibiotics, including a bismuth compound available over-the-counter as Pepto-Bismol. Normally, several antibiotic drugs are used together to prevent the bacteria from developing resistance to any one of them.

H. NSAID-Enteropathy/Enteritis

The anti-inflammatory, analgesic, and anti-pyretic properties of NSAIDs are well established and can be used in a wide range of disorders. The clinical utility of an any drug is determined by the compromise between its therapeutic efficacy and toxicity. If an NSAID is effective, but a patient cannot tolerate its side-effects then the NSAID is of no use to the patient. A major limitation of NSAIDs' clinical utility is their gastroduodenal epithelial toxicity. NSAID toxicity is not site-specific to the gastroduodenum, and can induce toxicity in the more distal intestine.

I. Infections

A variety of gastrointestinal infections also can be treated using the p40 and p75 proteins of the present invention. These include agents causing non-inflammatory gastroenteritis (*Staphylococcus aureus*, *Bacillus cereus*, *Clostridium perfringens*, and *Clostridium botulinum*), inflammatory gastroenteritis (*Vibrio cholerae*, enterotoxigenic *E. coli*, Enteropathogenic *E. coli*, Enteroaggregative *E. coli*, *Clostridium difficile*, *Vibrio parahemolyticus*, *Bacillus anhtracis*, rotavirus, noroviruses, *Giardia lamblia*, *Cryptosprodium parvum*, and *Cyclospora cavetanensis*), and invasive gastroenteritis (*Shigella* sp., *Salmonella* sp., *Campylobacter jejuni*, Enteroinvasive *E. coli*, Enterohemorrhagic *E. coli*, *Vibrio vulnificus*, *Yersinia* sp., *Francisella tularensis*, *Helibactor pylori* and *Entamoeba histolytica*. Such infections are treated with standard antibiotic and antibiotic combination treamtents.

IV. COMBINATION THERAPIES

A p40 or p75 composition may be administered in combination with another agent for the treatment of an epithelial cell disorder involving pathologic apoptosis. By combining agents, an additive effect may be achieved while not increasing the toxicity (if any) associated with a monotherapy. In addition, it is possible that more than additive effects ("synergism") may be observed. Thus, combination therapies are a common way to exploit new therapeutic regimens.

The p40 or p75 treatment may precede, be co-current with and/or follow the other agent(s) by intervals ranging from minutes to weeks. In embodiments where the p40 or p75 treatment and other agent(s) are applied separately to a cell, tissue or organism, one would generally ensure that a significant period of time did not expire between the time of each delivery, such that the p40 or p75 treatment and agent(s) would still be able to exert an advantageously combined effect on the cell, tissue or organism. For example, in such instances, it is contemplated that one may contact the cell, tissue or organism with two, three, four or more modalities substantially simultaneously (i.e. within less than about a minute) with the p40 or p75 treatment. In other aspects, one or more agents may be administered within of from substantially simultaneously, about 1 minute, about 5 minutes, about 10 minutes, about 20 minutes about 30 minutes, about 45 minutes, about 60 minutes, about 2 hours, about 3 hours, about 4 hours, about 5 hours, about 6 hours, about 7 hours about 8 hours, about 9 hours, about 10 hours, about 11 hours, about 12 hours, about 13 hours about 14 hours, about 15 hours, about 16 hours, about 17 hours, about 18 hours, about 19 hours, about 20 hours, about 21 hours, about 22 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 46 hours, about 47 hours, about 48 hours, about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 1, about 2, about 3, about 4, about 5, about 6, about 7 or about 8 weeks or more, and any range derivable therein, prior to and/or after administering the p40 or p75 treatment.

Various combination regimens of the p40 or p75 treatment and one or more agents may be employed. Non-limiting examples of such combinations are shown below, wherein a p40 or p75 treatment is "A" and an agent is "B":

| A/B/A   | B/A/B   | B/B/A   | A/A/B   | A/B/B   | B/A/A   |
|---------|---------|---------|---------|---------|---------|
| A/B/B/B | B/A/B/B | B/B/B/A | B/B/A/B | A/A/B/B | A/B/A/B |
| A/B/B/A | B/B/A/A | B/A/B/A | B/A/A/B | A/A/A/B | B/A/A/A |
| A/B/A/A | A/A/B/A |         |         |         |         |

Thus, p40 or p75 therapies of the present invention can be used in conjunction with other therapies that are used for the treatment of inflammatory bowel diseases (IBD) as discussed above.

V. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Materials and Methods

Bacterial Culture, LGG Broth Culture Supernatant (LGG-s), and LGG Conditioned Cell Culture Media (LGG-CM) Preparation.

*Lactobacillus rhamnosus* GG (ATCC 53103), *Lactobacillus casei* 334, (ATCC 334), *Lactobacillus casei* 393, (ATCC 393) and *Lactobacillus acidophilus* (ATCC 4356) were cultured in *Lactobacillus* MRS broth at 37° C. (Yan and Polk, 2002; Miettinen et al., 1996) according to ATCC guidelines. Bacteria were harvested from MRS broth by centrifugation and washed twice with phosphate-buffered saline (PBS). Following centrifugation, LGG-s was passed through a 0.2 μm filter. LGG-CM were generated by incubating LGG ($10^7$ CFU/ml) in RPMI or DMEM cell culture medium at 37° C. for 2 hours; the media were then centrifuged twice and the supernatant was filtered (0.2 μm).

Purification of Proteins from LGG Culture Supernatant.

To purify proteins under native conditions from LGG-s, LGG-s was loaded onto UNOsphere™ S ion exchange media (Bio-Rad Laboratories, Hercules, Calif.) which was prepared according to manufacturer's instructions. Bound proteins were eluted using 30 mM Tris, pH 7.3 containing sequential concentrations of NaCl (100 mM to 800 mM). Eluted fractions were collected and subjected to SDS-PAGE and stained with Colloidal Blue Stain kit (Invitrogen Corporation, Carlsbad, Calif.). Eluted fractions containing proteins were then concentrated using Amicon® Ultra-4 centrifugal filter devices (Millipore, Bedford, Mass.), with a 5 kDa molecular weight limit cut-off, and the >5 kDa molecular weight fraction was retained for study. Protein concentrations were determined by using a DC protein assay (Bio-Rad Laboratories). From 200 ml of LGG broth culture ($10^7$ CFU/ml), about 1 mg of p40 and 0.75 mg of p75 were purified. The concentration of purified proteins was adjusted to 0.1 mg/ml using PBS.

Antibody Generation and Immunodepletion of p75 and p40 from LGG-CM.

To prepare p75 and p40 as antigens for generating antibodies, chromatographically purified p75 and p40 were separated on an SDS-PAGE gel, and then p75 and p40 bands were excised and electro-eluted from the gels using a Model 422 Electro-Eluter (Bio-Rad Laboratories) according to the manufacture's instructions. SDS in the eluted fractions was removed by Bio-Beads® SM-2 adsorbents (Bio-Rad Laboratories). Polyclonal antibodies against p75 and p40 were generated by injecting rabbits with purified p75 or p40 proteins, respectively (Strategic Biosolutions, Newark, Del.). p75 and p40 antibodies were conjugated to Protein A/G beads (Santa Cruz Biotechnology, Santa Cruz, Calif.) by incubating antibodies with beads in PBS for 2 hours at 4° C. To sequentially immunodeplete p75 and p40 from LGG-CM, LGG-CM was incubated with anti-p75 antibody-conjugated beads for 4 hours at 4° C. After removing anti-p75 antibody-conjugated beads, CM was incubated with anti-p40 antibody-conjugated beads for another 4 hours. Preimmune serum was used as the negative control. The amounts of p75 and p40 present in LGG-CM or immunodepleted LGG-CM were detected by Western blot analysis with anti-p75 and anti-p40 antibodies.

N-Terminal and Internal Peptide Sequence Analysis of p75 and p40.

p75 and p40 proteins were purified as described above, separated by SDS-PAGE, and transferred to a PVDF membrane (Bio-Rad Laboratories, Inc). N-terminal peptide sequence analysis of p75 and p40 by Edman degradation methodology was performed at Iowa State University Protein Facility (Ames, Iowa). Internal peptide sequences of p75 and p40 were determined by performing in-gel digestion of the proteins with trypsin, followed by analysis of the resulting peptides by matrix-assisted laser desorption/ionization, time-of-flight mass spectrometry (MALDI-TOF/MS/MS), and liquid chromatography-tandem mass spectrometry (LC/MS/MS) at the Vanderbilt University Proteomics Core of the Digestive Disease Research Center, Nashville, Tenn.

Analysis of the LGG Genes Encoding p75 and p40.

N-terminal and internal peptide sequences of p75 and p40 were compared with protein sequences in the NCBI microbial genome database using BLAST analysis. The most closely related proteins were encoded by two genes in the genome of Lactobacillus casei 334 (Genbank accession numbers COG0791 and COG3883). Multiple primer pairs were designed based on the sequences of these L. casei genes and flanking DNA sequences in the L. casei genome. LGG genomic DNA was isolated using the Wizard® Genomic DNA Purification Kit (Promega Corporation, Madison, Wis.), and this DNA was used as a template for PCR. PCR was carried out for 30 cycles, each including 30 seconds at 95° C., 30 seconds at 55° C., and 30 seconds at 72° C. PCR products were excised from agarose gels and purified using a QIAquick Gel Extraction Kit (QIAGEN Company, Valencia, Calif.). PCR products were cloned into pGEM®-T Easy vector (Promega Corporation), plasmids were transformed into E. coli DH5α, and the nucleotide sequences were then determined.

Cell Culture and Cell Treatment.

Young adult mouse colon (YAMC) epithelial cells or kinase suppressor of Ras knock-out ($KSR^{-/-}$) mouse colon epithelial (MCE) cells were maintained in RPMI 1640 media with 5% FBS and 5 U/ml of murine interferon (IFN)-γ on collagen-coated plates and grown under permissive conditions at 33° C. with 5% $CO_2$ (Yan et al., 2004). Before all experiments, cells were transferred to 37° C. (non-permissive) conditions with 0.5% FBS, IFN-γ-free media for 16 hours. The human colonic epithelial carcinoma cell line, HT 29 cells, was grown in DMEM media supplemented with 10% FBS at 37° C. Cells were serum-starved (0.5%) at 37° C. for about 16 hours before experiments. Cells were treated with purified p75, p40, LGG-CM or $10^7$ CFU/ml of bacteria (20:1 ratio of bacteria to cells) for 2 hours, or 1 hour before TNF (100 ng/ml) treatment. To compare the effects of soluble factors, cells were cultured in transwells with bacteria placed in the upper chamber, separated by a permeable filter (0.2 μm pore size).

Preparation of Cellular Lysates.

After treatment, cell monolayers were washed twice with ice-cold PBS and then scraped into cell lysis buffer [20 mM HEPES (pH 7.5), 1 mM orthovandate, 50 mM β-glycerol-phosphate, 10 mM sodium pyrophosphate, with leupeptin (10 μg/ml), aprotinin (10 μg/ml), PMSF (18 μg/ml), and 1% Triton-X-100]. The scraped suspensions were centrifuged (14,000×g, 10 min) at 4° C. and protein content was determined using DC protein assay (Bio-Rad Laboratories). Cellular lysates were mixed with Laemmli sample buffer and proteins were separated by SDS-PAGE for Western blot analysis with anti-p75, anti-p40, anti-phospho-Ser 473 (P)-Akt, anti-Akt, anti-phospho-Tyr180/182 (P)-p38 MAPK, anti-inhibitor of nuclear factor κB(IκB)α (Cell Signaling Technology, Beverly, Mass.), and anti-phospho-Thr183/Tyr185 (P)-extracellular signal-regulated kinase (ERK)1/2 MAPK (Promega, Madison, Wis.).

Colon Organ Culture.

All animal experiments were performed according to protocols approved by the Institutional Animal Care and Use Committee at Vanderbilt University. 6-8 week old C57BL/6 mice were sacrificed, the colon was opened and washed with sterile PBS and DMEM media, and then cut into 4×4 mm pieces. The colon explants were laid on Netwell™ inserts (membrane mesh size of 500 μM, Corning Incorporated Life Sciences, Acton, Mass.) with the serosal layer facing the insert. DMEM containing 0.5% FBS was filled to a point just over the epithelium and incubated at 37° C. with 5% $CO_2$ for 2 hours before treatment. At the end of the experiment, colon tissue was fixed in 4% paraformaldehyde at 4° C. overnight before sectioning. Paraffin-embedded tissue sections were stained with hematoxylin and eosin for light microscopic assessment of epithelial injury, or for apoptosis assays.

Apoptosis Assays.

Apoptosis was detected in colon tissue slides by ApopTag™ In Situ Oligo Ligation (ISOL) Kit (Intergen Company, Purchase, N.Y.) using T4 DNA ligase according to the manufacturer's guidelines, or by using anti-active caspase-3 antibody (BD Biosciences, Palo Alto, Calif.)

staining and reagents provided in the Vectastain ABC kit (Vector Laboratories, Inc., Burlingame, Calif.). Differential interference contrast (DIC) microscopy was used as the inventors have previously reported (Yan et al., 2004). Apoptotic cells were determined by counting the absolute number of positive stained cells in at least 300 colonic crypts.

Apoptosis in cell lines was detected by two methods. ApopTag In Situ Apoptosis Detection Kits (TUNEL, Intergen Company, Purchase, N.Y.) and DAPI staining were described previously (Yan et al., 2004; Yan et al., 2001). The slides were observed by fluorescence microscopy, and the number of positively stained cells within a population of at least 500 cells was counted in order to determine the proportion of apoptotic cells. For Annexin V-FITC staining, attached cells were dissociated using Accutase (Innovative Cell Technologies, Inc. San Diego, Calif.) and double stained with Annexin V-FITC and propidium iodide (Calbiochem/EMD Biosciences, Darmstadt, Germany) according to the respective manufacturer's instructions. The percentage of cells positive for Annexin V and propidium iodide was determined by flow cytometry.

Cell Proliferation Assays.

After YAMC cells cultured in 96-well dishes were treated with LGG, purified p75, or purified p40 for 24 hours, cells were incubated with CellTiter 96® AQ$_{ueous}$ One Solution Reagent (Promega Corp., Madison, Wis.) for 1 hour to label viable cells. The absorbance at 590 mm was detected using a 96-well plate reader. Cell numbers were determined by comparing the absorbance of samples to the standard cell-absorbance curve generated for each experiment. The change in the number of control cells from the start to the end of an experiment was standardized as 100%. The changes in the treated cells were reported as a percentage relative to the untreated control.

Cell proliferation was also determined by immunostaining of cells on chamber slides with anti-proliferative cell nuclear antigen (PCNA) antibody (Santa Cruz Biotechnology, Santa Cruz, Calif.) using reagents provided in the Vectastain ABC kit (Vector Laboratories, Inc., Burlingame, Calif.) and visualization of cells by DIC microscopy. At least 500 cells were counted to determine the percentage of cells with positive PCNA nuclei.

Statistical Analysis.

The statistical significance of the difference between mean values was determined using paired Student's t test analysis. The level of statistical significance was set at $p<0.05$. Data were analyzed as the mean±SD.

Example 2—Results

Purification of Two Proteins, p75 and p40, from LGG Culture Supernatant.

Soluble factors recovered from LGG-s and LGG-CM have been shown to regulate intestinal epithelial signaling pathways and biological functions (Yan and Polk, 2002; Tao et al., 2006), but the identities of these factors are unknown. Therefore, the inventors pursued characterization of these soluble factors to provide insight into the molecular mechanisms of probiotic bacterial actions on host cells. As a first step, proteins in the culture supernatant of LGG broth cultures were analyzed by SDS-PAGE and Coomassie blue staining. Two of the most abundant proteins had molecular masses of about 75 kDa and 40 kDa. To purify these proteins from LGG-s, filtered LGG-s was loaded onto UNOsphere™ S ion exchange media with negatively charged functional groups, and bound proteins were eluted using 30 mM Tris (pH 7.3) containing progressively increasing concentrations of NaCl from 0.1 M to 0.8 M. Eluted proteins were analyzed by SDS-PAGE to identify proteins contained in each fraction (data not shown). The 75 kDa protein (p75) and 40 kDa protein (p40) eluted from the cation exchange resin at NaCl concentrations of 0.25 M and 0.5 M, respectively (FIG. 1A). SDS-PAGE analysis indicated that the chromatography procedure successfully separated p75 and p40.

Anti-p75 and anti-p40 polyclonal antibodies were generated using chromatographically purified p75 or p40 respectively. Western blot analysis indicated that the anti-p75 antiserum recognized p75 only (FIG. 1B), and the anti-p40 antiserum reacted with both p40 and p75 (FIG. 1C). Preimmune sera did not react with either p75 or p40 (FIGS. 1B-C). Immunoblotting experiments indicated that the purified p75 preparation was not contaminated with p40, and the purified p40 preparation was not contaminated with p75 (FIG. 1B-C).

Characterization of p75 and p40 Proteins.

As a first step in characterizing p75 and p40, N-terminal sequences and internal peptide sequences of these proteins were determined, as described in the Methods. When compared with sequences in the NCBI microbial genome database, the p75 and p40 peptide sequences were most closely related to two proteins predicted to be encoded by the genome of *L. casei* 334 (NCBI GeneBank accession numbers COG0791 and COG3883, respectively). Multiple oligonucleotide primers were designed based on the sequences of the corresponding *L. casei* genes and flanking DNA sequences in the *L. casei* genome, and these primers were used to PCR-amplify related sequences from LGG genomic DNA.

Sequence analysis of one set of cloned PCR products revealed the presence of a 1236 bp ORF, predicted to encode a 412 amino acid residue protein with a calculated molecular mass of 42 kDa (FIG. 1D). The experimentally determined N-terminal amino acid sequence of LGG p40, as well as an internal peptide sequence of p40, were identified within the deduced amino acid sequence encoded by this ORF (FIG. 1D). The deduced full-length amino acid sequence of p40 was 79% identical to the sequence of a 396 amino acid protein of unknown function in *L. casei* 334 (NCBI GeneBank COG3883).

Sequence analysis of another set of cloned PCR products revealed the presence of a partial ORF that was >1488 bp in length; the full-length ORF was not successfully amplified. The experimentally determined N-terminal amino acid sequence of p75 and internal peptide sequences of p75 were identified within the deduced amino acid sequence encoded by this partial ORF (FIG. 1D). The deduced amino acid sequence of p75 was most closely related to a 493-amino-acid cell wall-associated hydrolase of *L. casei* 334 (NCBI GeneBank COG0791), and exhibited 70% and 93% identity to two different regions of this *L. casei* 334 protein. The predicted molecular mass of the full-length cell wall-associated hydrolase of *L. casei* 334 (49 kDa) differs substantially from the molecular mass of the LGG p75 protein.

An analysis of the LGG p40 and p75 gene sequences and the experimentally determined N-terminal amino acid sequences of the encoded proteins indicates that both genes encode proteins with N-terminal signal sequences. The presence of signal sequences is consistent with the hypothesis that p40 and p75 are actively secreted into the culture supernatant by LGG. The p40 gene sequence and the partial p75 gene sequence do not show significant relatedness, and the experimentally determined N-terminal amino acid sequences of these two proteins are not related. Thus, based on the available sequence data, there is no evidence to suggest that p40 is a degradation product of p75. However, it is possible that there could be sequence similarity between p40 and the uncharacterized C-terminal portion of p75.

p75 and p40 Stimulate Akt Activation in Intestinal Epithelial Cells.

Because the inventors have reported that factors recovered from LGG-s stimulate Akt activation (Yan and Polk, 2002), they first determined the effect of p75 and p40 on this signal transduction pathway. Cells were treated with various concentrations of p75 and p40 and activation of Akt was determined by Western blot analysis using an antibody against phosphorylated Akt. The inventors found that p75 at 10-1000 ng/ml and p40 at 1-100 ng/ml stimulated Akt activation in a concentration-dependent manner in either mouse or human colon epithelial cells (FIG. 2A). p75 at 100 ng/ml and p40 at 10 ng/ml were chosen for subsequent experiments in this paper because these are the minimal concentrations for inducing detectable Akt activation. As controls, the inventors tested the flow-through fraction from the ion exchange column and the fraction eluted from the column with 0.1 M NaCl; neither of these preparations contained p75 or p40, and neither of these preparations activated Akt (data not shown). As with LGG-s, Akt activation by p75 or p40 was PI3K-dependent because PI3K inhibitors, LY294002 and Wortmannin (data not shown) blocked p75 and p40 activation of Akt (FIG. 2B). As the inventors have previously reported that LGG, but not LGG-CM, inhibits TNF-stimulated activation of p38 (Yan and Polk, 2002), they tested whether the purified LGG-s proteins modulate this signaling pathway. Similar to LGG-CM, p75 and p40 showed no effect on TNF activation of p38 (FIG. 2D). Furthermore, p75 and p40 were also not able to induce ERK1/2 or p38 activation or IκBα degradation (15 min to 4 hour treatments, 2-hour treatment data are shown in FIG. 2D), or inhibit TNF's effects on these pathways (FIG. 2D). Therefore, purified p75 and p40 are selective in their activity for regulating intestinal epithelial cell signal transduction.

p75 and p40 Inhibit TNF-Induced Intestinal Epithelial Cell Apoptosis and Organ Culture Lesions.

To determine the biological roles of purified proteins from LGG-s, the inventors next evaluated the effects of p75 and p40 on cytokine-induced apoptosis in intestinal epithelial cells. The inventors detected intestinal epithelial cell apoptosis and distinguished it from necrosis by using three different methods. TUNEL and ISOL assays measure apoptosis by specifically labeling fragmented genomic DNA with terminal deoxynucleatidyl transferase or T4 DNA ligase, respectively Annexin V staining detects apoptosis based on FITC-conjugated Annexin V specifically binding to phosphatidylserine once it is exposed to the outer layer of the plasma membrane during the apoptotic process (van Engeland et al., 1998).

TNF-induced apoptosis detected by TUNEL assay in KSR$^{-/-}$MCE cells, a mouse colon cell line null for KSR expression which undergoes apoptosis following TNF treatment (Yan et al., 2004), was inhibited by either p75 or p40 (FIGS. 3A-B). As expected, TNF-induced apoptosis was also inhibited by LGG co-culture (Yan and Polk, 2002). These results were confirmed in HT29 cells, a human intestinal cell line by Annexin V-FITC staining. The "cytokine cocktail" combination of TNF, interleukin (IL)-1α, and IFN-γ induced apoptosis in HT29 cells which was reversed by either p75 or p40 treatment (FIGS. 3C-D).

To determine the potential of p75 and p40 to regulate colon epithelial homeostasis, the inventors performed colon organ culture and observed the direct effects of p75 and p40 on colon epithelium ex vivo as detailed in Methods. Histological sections prepared for injury assessment showed that TNF induced massive mucosal necrosis and disruption of epithelial integrity in colon explants. Co-culture with p75, p40 or LGG with TNF restored colonic epithelial integrity and the crypt structure of the colon crypts (FIG. 4).

Figure 5:
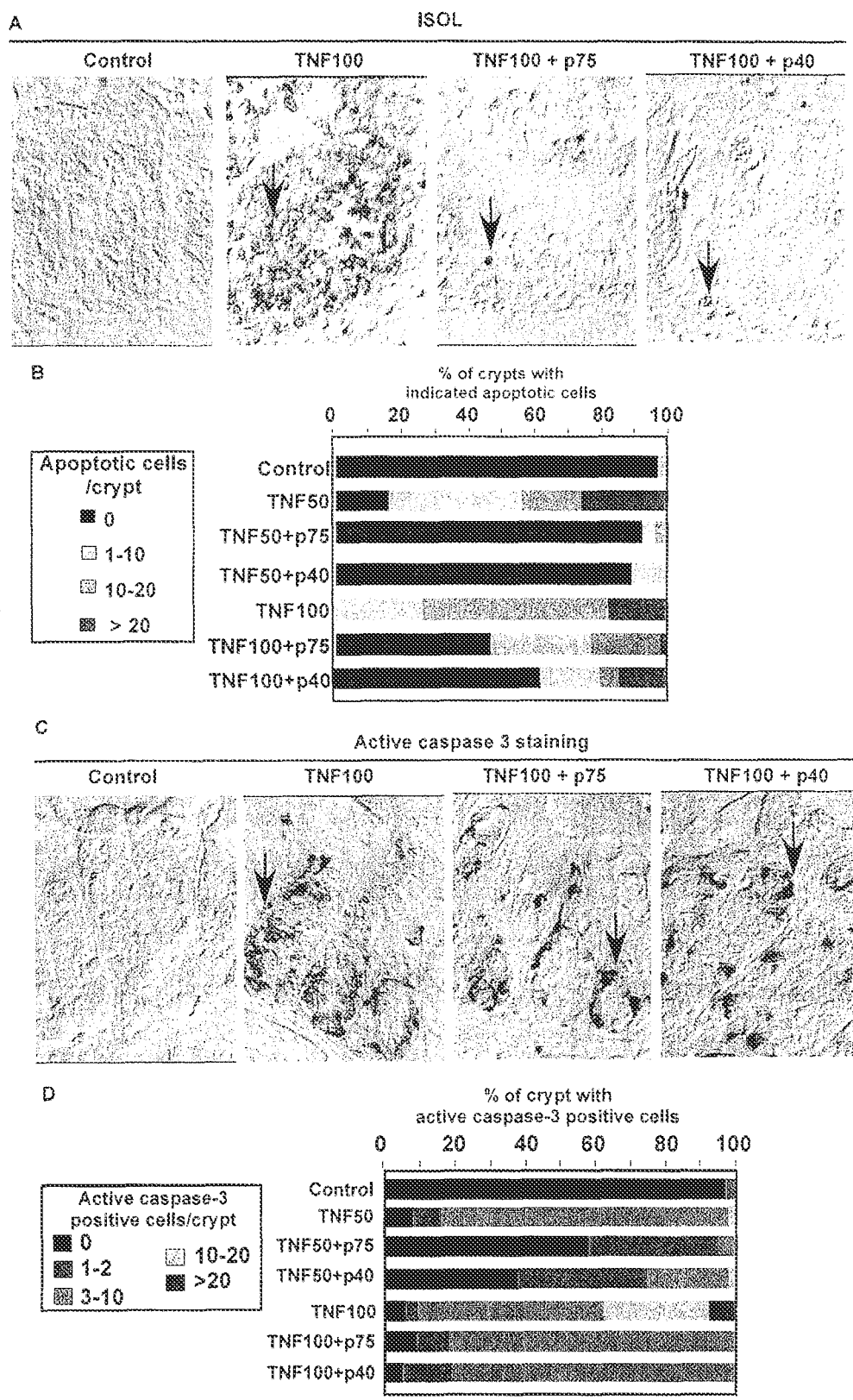
FIGS. 5A-D—p75 and p40 inhibit TNF-induced apoptosis in cultured mouse colon explants. Mouse colon explants prepared as in FIG. 4 were treated with TNF (50 ng/ml, TNF50 or 100 ng/ml, TNF100) for 24 hours in the presence or absence of LGG, p75 (100 ng/ml) or p40 (10 ng/ml). Paraffin-embedded tissue sections were studied for apoptosis using ISOL staining Apoptotic nuclei labeled with peroxidase were visualized using DIC microcopy (FIG. 5A). Caspase-3 activity was determined by immunohistochemistry using anti-active caspase-3 antibody (FIG. 5C). The percentage of crypts with indicated apoptotic nuclei (FIG. 5B) or positive active caspase 3 (FIG. 5D) cells is shown. Arrows indicate examples of ISOL or caspase-3 positive cells. The percentage shown here is the average representing five independent experiments. All images in this figure were taken with 40× magnification.

Co-culture of colon tissue explants with TNF induced colon epithelial apoptosis with 75% of crypts containing more than 10 apoptotic cells. This effect was decreased 3-fold by p75 or p40 co-treatment ($p<0.005$, FIGS. 5A-B). Because caspase 3 is a major regulator of the apoptotic program, and PI3K-dependent Akt activation has been shown to prevent TNF induced caspase 3 activation (Trencia et al., 2003), the inventors determined the effect of p75 and p40 on caspase 3 activity using immunostaining with an anti-active caspase 3 antibody. TNF stimulated caspase 3 activation in intestinal epithelial cells, which was significantly inhibited by p75 or p40 co-culture (FIGS. 5C-D).

Thus, in mouse and human intestinal epithelial cell lines and cultured mouse colon explants using three different apoptotic assays, both p75 and p40 exert significant inhibitory effects on TNF-induced apoptosis. These effects may be involved in protective roles on TNF-induced intestinal epithelial lesions.

p75 and p40 Stimulate Intestinal Epithelial Cell Growth.

Figure 6:
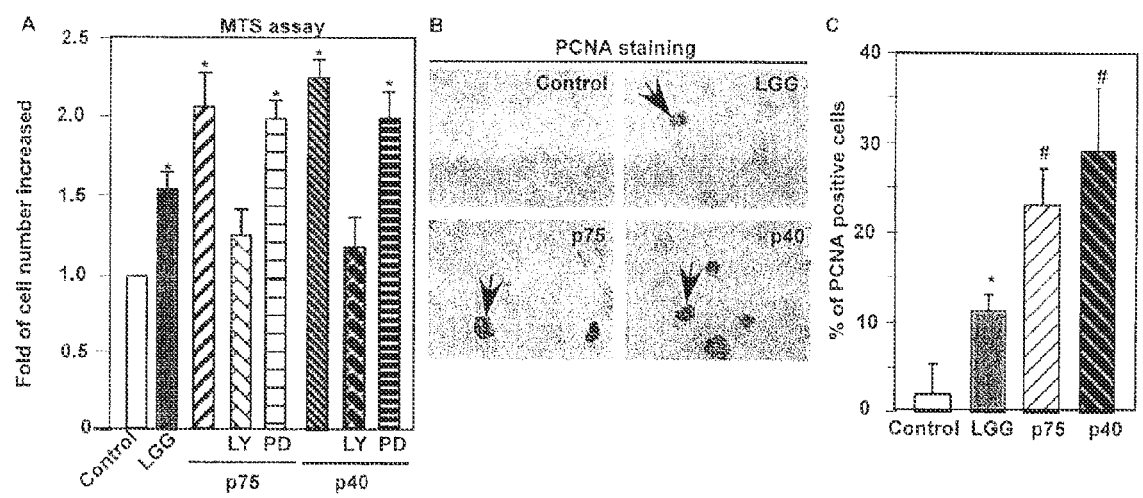
FIGS. 6A-C—p75 and p40 promote intestinal epithelial cell proliferation. YAMC cells plated in 96-well dish were treated with LGG, p74 (100 ng/ml), or p40 (10 ng/ml) for 24 hours. At the end of treatment, viable cells were counted using MTS-based assays. The change in the number of control cells from the start to the end of a experiment was standardized as 100%. Changes in the treated cells were reported as a percentage relative to the untreated control (FIG. 6A). Cells cultured on chamber slides treated as indicated were immunostained with anti-proliferative cell nuclear antigen (PCNA) antibody. Peroxidase-labeled positive cells, indicated by arrows, were observed by DIC microscopy (FIG. 6B). At least 500 cells were counted to determine the percentage of PCNA positive cells (FIG. 6C). *, $p<0.01$, #, $p<0.001$ compared with control. Data in this figure represent at least three separate experiments.

The homeostatic balance between proliferation and apoptosis regulates normal gastrointestinal epithelial morphology and function. Probiotic bacteria have been shown to enhance intestinal epithelial cell proliferation (Ichikawa et al., 1999). Furthermore, PI3K and Akt have been reported to play a critical role in regulating this proliferative response in intestinal epithelial cells (Sheng et al., 2003). Therefore, the inventors evaluated the effects of p75 and p40 on cellular proliferation using an MTS-based proliferation assay. Both p75 and p40 promoted YAMC cell growth, which was inhibited by the PI3K inhibitor, LY294002, but not the MEK inhibitor, PD98059 (FIG. 6A). To further characterize p75 and p40's effects on intestinal cellular proliferation, PCNA staining was used to detect proliferative nuclei. p75 and p40 enhanced the number of PCNA-positive nuclei (FIGS. 6B-C). These results suggest that p75 and p40 help to restore intestinal epithelial integrity after TNF-induced injury through not only preventing apoptosis, but also enhancing proliferation.

Immunodepletion of p75 and p40 from LGG-CM Blocks LGG-CM's Biological Effects on Intestinal Epithelial Cells.

Figure 7:
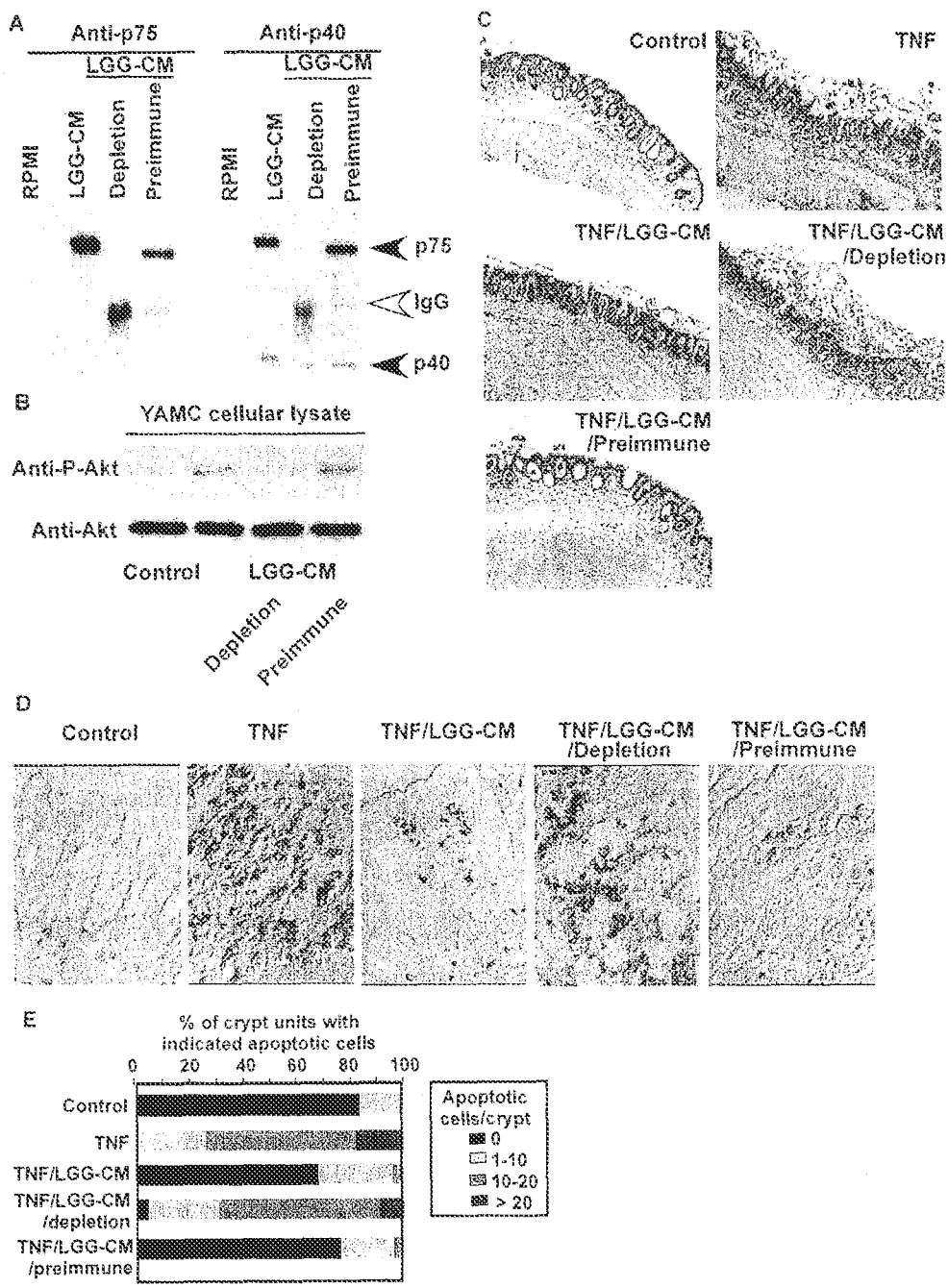
FIGS. 7A-E—Immunodepletion of p75 and p40 blocks LGG-conditioned cell culture media (CM)'s anti-apoptotic effects on colon epithelial cells. Immunodepletion of p75 and p40 was performed by sequential immunoprecipitation of LGG-CM with anti-p75 and p40 antibodies, characterized in FIGS. 1A-D, to remove both p75 and p40 from LGG-CM. Preimmune sera were used as a control. Proteins present in LGG-CM, LGG-CM immunodepleted with antibodies (LGG-CM depletion) or preimmune sera (LGG-CM preimmune) were separated by SDS-PAGE for Western blot analysis with anti-p75 and p40 antibodies (FIG. 7A). LGG-CM, LGG-CM depletion and LGG-CM preimmune were used to treat YAMC cells to detect Akt activation as shown in FIGS. 2A-D (FIG. 7B), or C57BL/6 mouse colon explants described as in FIGS. 5A-D in the presence or absence of TNF (100 ng/ml) for 24 hrs. Paraffin-embedded tissue sections were stained with hematoxylin and eosin for light microscopic assessment of epithelial damage (FIG. 7C, 10× magnification), and ISOL staining to detect epithelial cell apoptosis using DIC microscopy (FIG. 7D, 40× magnification). The percentage of crypts with indicated apoptotic cells is shown (FIG. 7E). Data represent mean scores from at least three experiments.

To test by another approach whether p75 and p40 are required for the regulatory effects of LGG-CM on intestinal epithelial cells, antibodies against p75 and p40 were used for sequential immunoprecipitation to immunodeplete both p75 and p40 from LGG-CM. Immunoprecipitation with these two antibodies, but not preimmune sera, efficiently removed p75 and p40 from LGG-CM (FIG. 7A). These immunodepleted LGG-CM fractions were used to treat cells or colon culture explants. Immunodepletion of p75 and p40 from LGG-CM attenuated Akt activation (FIG. 7B). Furthermore, LGG-CM, but not immunodepleted LGG-CM, prevented TNF-induced ulcerative lesions, including mucosal necrosis and disruption of epithelial integrity (FIG. 7C) and epithelial apoptosis in colon organ cultures (FIGS. 7D-E). Individual immunodepletion of either p75 or p40 partially attenuated Akt activation and the anti-apoptotic response (data not shown). These results indicate that p75 and p40 are required for LGG-CM regulation of intestinal epithelial cells and suggest that they may have redundant functions.

Strain-Specific Expression of p75 and p40 by Lactobacilli.

Because the inventors have reported that probiotic Lactobacilli regulation of cell survival is strain-specific (Yan and Polk, 2002), the inventors next investigated whether expression of soluble p75 and p40 proteins was also strain-specific. To address this question, they studied three other strains of *Lactobacillus*, *Lactobacillus casei* 334, *Lactobacillus casei* 393, and *Lactobacillus acidophilus*, which are known to regulate intestinal function (Resta-Lenert and Barrett, 2006; Tien et al., 2006) or lymphocyte proliferation and immunity (Gill et al., 2000). Conditioned-media derived proteins from $10^5$ of these respective *Lactobacillus* strains were separated by SDS-PAGE (FIG. 8A). p75 and p40 antisera recognized proteins of similar size in culture supernatant from *L. casei* 393-CM, but no immunoreactive proteins were detected in culture supernatant from *L. acidophilus*-CM (FIG. 8B). The p40 antiserum recognized a 38 kDa protein produced by *L. casei* 334-CM (FIG. 8B), which is consistent with relatedness between LGG p40 and a protein of unknown function encoded by *L. casei* (NCBI GeneBank COG3883). Weak reactivity of the p75 antiserum with a 75 kDa *L. casei* protein was detectable only if films were overexposed (data not show).

To investigate the effects of soluble factors produced by these *Lactobacillus* species on epithelial cells, bacteria were co-cultured with the epithelial cells but were physically separated by a filter (0.2 µM), so that any observed effects would be mediated by soluble factors. Although all of the strains stimulated Akt activation and inhibited cytokine-induced apoptosis when in direct contact with epithelial cells, LGG, *L. casei* 334, and *L. casei* 339, but not *L. acidophilus* supernatants promoted Akt activation (FIG. 8C) and prevented TNF-induced apoptosis (FIG. 8D). Strain-specific production of soluble p75 and p40 proteins and the correlation between expression of these proteins and observable phenotypes provides further evidence that these bacterial components can promote intestinal epithelial cell survival and inhibit cytokine-induced apoptosis.

p75 and p40 Stimulate Epidermal Growth Factor (EGF) Receptor Activation which Regulates Akt in Intestinal Epithelial Cells.

Figure 9:
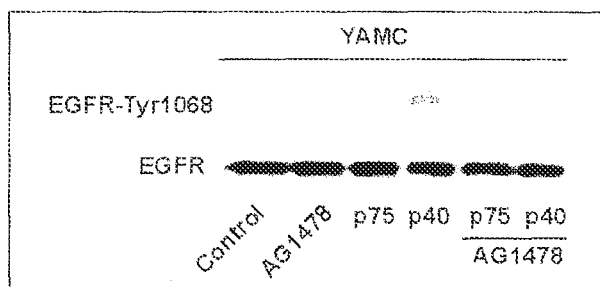
FIGS. 9—p75 and p40 activate EGF receptor in YAMC cells. Cells were treated with p75 (100 ng/ml) or p40 (10 ng/ml) for 1 hr in the presence or absence of 30-min pretreatment of tyrosine kinase inhibitor, AG1478 (10 nM). Cellular lysates were collected for Western blot analysis to detect EGF receptor activation using anti-EGFR-phospho-Tyr1068 antibody, and EGFR receptor expression using anti-EGFR antibody.

EGF receptor signaling is a known upstream regulator for PI3K activation which leads to Akt activation. Therefore, we tested the requirement of EGF receptor in p75 and p40 activation of Akt. We found that p75 and p40 stimulate EGF receptor activation in young adult mouse colon (YAMC) cells, which is inhibited by EGF receptor tyrosine kinase inhibitor, AG1478 (FIG. 9). Furthermore, p75 and p40 fail to activate Akt in EGF receptor knock out (EGFR$^{-/-}$) mouse colon epithelial (MCE) cells (FIG. 10A), which is rescued by wild-type (wt) EGF receptor, but not kinase inactive (ki) EGF receptor re-expression in MCE cells (FIG. 10B). These results indicate that EGF receptor may mediate p75 and p40 regulating Akt activation in intestinal epithelial cells.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,554,101
U.S. Pat. No. 4,684,611
U.S. Pat. No. 4,797,368
U.S. Pat. No. 4,879,236
U.S. Pat. No. 4,952,500
U.S. Pat. No. 5,139,941
U.S. Pat. No. 5,302,523
U.S. Pat. No. 5,322,783
U.S. Pat. No. 5,384,253
U.S. Pat. No. 5,384,253
U.S. Pat. No. 5,440,013
U.S. Pat. No. 5,443,826
U.S. Pat. No. 5,446,128
U.S. Pat. No. 5,464,765
U.S. Pat. No. 5,475,085
U.S. Pat. No. 5,538,877
U.S. Pat. No. 5,538,880
U.S. Pat. No. 5,550,318
U.S. Pat. No. 5,563,055
U.S. Pat. No. 5,580,859
U.S. Pat. No. 5,589,466
U.S. Pat. No. 5,591,616
U.S. Pat. No. 5,599,795
U.S. Pat. No. 5,610,042
U.S. Pat. No. 5,618,914
U.S. Pat. No. 5,656,610
U.S. Pat. No. 5,670,155
U.S. Pat. No. 5,672,681
U.S. Pat. No. 5,674,976
U.S. Pat. No. 5,702,932
U.S. Pat. No. 5,710,245
U.S. Pat. No. 5,736,524
U.S. Pat. No. 5,780,448
U.S. Pat. No. 5,789,215
U.S. Pat. No. 5,840,833
U.S. Pat. No. 5,859,184
U.S. Pat. No. 5,871,986
U.S. Pat. No. 5,929,237
U.S. Pat. No. 5,945,100
U.S. Pat. No. 5,981,274
U.S. Pat. No. 5,994,136
U.S. Pat. No. 5,994,624
U.S. Pat. No. 6,013,516
Amaravadi and Thompson, *J. Clin. Invest.*, 115:2618-2624, 2005.
Apostolou et al., *FEMS Immunol. Med. Microbiol.*, 31:35-39, 2001.
Ausubel et al., In: *Current Protocols in Molecular Biology*, John, Wiley & Sons, Inc, N Y, 1994.
Baichwal and Sugden, In: *Gene Transfer*, Kucherlapati (Ed.), Plenum Press, NY, 117-148, 1986.
Bates, *Mol. Biotechnol.*, 2(2):135-145, 1994.
Battraw and Hall, *Theor. App. Genet.*, 82(2):161-168, 1991.
Besnard et al., Besnard et al., *Gut.*, 43(5):634-638, 1998.
Bhattacharjee et al., *J. Plant Bioch. Biotech.*, 6(2):69-73. 1997.

Blomer et al., *J. Virol.*, 71(9):6641-6649, 1997.
Borody et al., *J. Clin. Gastroenterol.*, 37:42-47, 2003.
Botoman et al., *Am. Fam. Physician*, 57(1):57-68, 1998.
Bousvaros et al., *Inflamm. Bowel Dis.*, 11:833-839, 2005.
Brynskov et al., *N. Engl. J. Med.*, 321(13):845-850, 1989.
Carbonelli et al., *FEMS Microbiol. Lett.*, 177(1):75-82, 1999.
Chandler et al., *Proc. Natl. Acad. Sci. USA*, 94(8):3596-601, 1997.
Chen and Okayama, *Mol. Cell Biol.*, 7(8):2745-2752, 1987.
Christou et al., *Proc. Natl. Acad. Sci. USA*, 84(12):3962-3966, 1987.
Cocea, *Biotechniques*, 23(5):814-816, 1997.
Cotten et al., *Proc. Natl. Acad. Sci. USA*, 89(13):6094-6098, 1992.
Coupar et al., *Gene*, 68:1-10, 1988.
Curiel, *Nat. Immun.*, 13(2-3):141-164, 1994.
D'Halluin et al., *Plant Cell*, 4(12):1495-1505, 1992.
Dieleman et al., *Gut.*, 52:370-376, 2003.
Dionne et al., *Clin. Exp. Imunol.*, 112(3):435-442, 1998.
Dotan et al., *Curr. Opin. Gastroenterol.*, 21:426-430, 2005.
El-Assal and Besner, *Gastroenterology*, 129:609-625, 2005.
EPO 0273085
Fechheimer et al., *Proc Natl. Acad. Sci. USA*, 84:8463-8467, 1987.
Fellerman et al., *Am. J. Gastroenterol.*, 93(10):1860-1866, 1998.
Fraley et al., *Proc. Natl. Acad. Sci. USA*, 76:3348-3352, 1979.
Friedmann, *Science*, 244:1275-1281, 1989.
Funakoshi et al., *Digestion*, 59(1):73-78, 1998.
Galley and Webster, *Br. J. Anaesth.*, 77:11-16, 1996.
Gill et al., *Br. J. Nutr.*, 83:167-176, 2000.
Gopal, *Mol. Cell Biol.*, 5:1188-1190, 1985.
Graham and Van Der Eb, *Virology*, 52:456-467, 1973.
Grunhaus and Horwitz, *Seminar in Virology*, 3:237-252, 1992.
Hanada et al., *Biochim. Biophys. Acta*, 1697:3-16, 2004.
Harland and Weintraub, *J. Cell Biol.*, 101(3):1094-1099, 1985.
He et al., *Plant Cell Reports*, 14 (2-3):192-196, 1994.
Hoffenberg et al., *J. Pediatr.*, 134(4):447-452, 1999.
Hollander et al., *Ann. Intern. Med.*, 105:883-885, 1986.
Hollander, *Scand. J. Gastroenterol.*, 27:721-726, 1992.
Hooper et al., *Science*, 291:881-884, 2001.
Horwich et al. *J. Virol.*, 64:642-650, 1990.
Hou and Lin, *Plant Physiology*, 111:166, 1996.
Ichikawa et al., *Dig. Dis. Sci.*, 44:2119-2123, 1999.
Inouye and Inouye, *Nucleic Acids Res.*, 13:3101-3109, 1985.
Johannesson et al., *J. Med. Chem.*, 42(22):4524-4537, 1999.
Johnson et al., *In: Biotechnology And Pharmacy*, Pezzuto et al. (Eds.), Chapman and Hall, N Y, 1993.
Kaeppler et al., *Plant Cell Reports*, 9:415-418, 1990.
Kaneda et al., *Science*, 243:375-378, 1989.
Kato et al, *J. Biol. Chem.*, 266:3361-3364, 1991.
Kelleher and Vos, *Biotechniques*, 17(6):1110-7, 1994.
Kelly et al., *Nat. Immunol.*, 5:104-112, 2004.
Klein et al., *Nature*, 327:70-73, 1987.
Knodler et al., *J. Biol. Chem.*, 280:9058-9064, 2005.
Kuboyama, *Kurume Med. J.*, 45(1):33-37, 1998.
Land et al., *Pediatrics*, 115:178-181, 2005.
Laughlin et al., *J. Virol.*, 60(2):515-524, 1986.
Lazzeri, *Methods Mol. Biol.*, 49:95-106, 1995.
Lebkowski et al., *Mol. Cell. Biol.*, 8(10):3988-3996, 1988.
Lee et al., *Environ. Mol. Mutagen.*, 13(1):54-59, 1989.
Leiper et al., *Baillieres Clin. Gastroenterol.*, 12(1):179-199, 1998.
Levenson et al., *Hum. Gene Ther.*, 9(8):1233-1236, 1998.
Lilly and Stillwell, *Science*, 147:747-748, 1965.
Lugering et al., *Ital. J. Gastroenterol. Hepatol.*, 30(3):338-344, 1998.
Mack et al., *Gut.*, 52:827-833, 2003.
Macpherson and Uhr, *Science*, 303:1662-1665, 2004.
Makowiec et al., *Z. Gastroenterol.*, 36(8):619-624, 1998.
Maniatis, et al., Molecular Cloning, A Laboratory Manual, Cold Spring Harbor Press, Cold Spring Harbor, N.Y., 1989.
Mann et al., *Cell*, 33:153-159, 1983.
Marini et al., *Proc. Natl. Acad. Sci. USA*, 100:8366-8371, 2003.
Matsuura et al., *Gastroenterology*, 128:975-986, 2005.
McAlindon et al., *Gut.*, 42(2):214-219, 1998.
McCole et al., *Gastroenterology*, 129:591-608, 2005.
McLaughlin et al., *J. Virol.*, 62(6):1963-1973, 1988.
Miettinen et al., *Infect. Immun.*, 64:5403-5405, 1996.
Miller et al., *Am. J. Clin. Oncol.*, 15(3):216-221, 1992.
Mimura et al., *Gut.*, 53:108-114, 2004.
Murch, *Nutrition*, 14:780-783, 1998.
Muzyczka, *Curr. Topics Microbiol. Immunol.*, 158:97-129, 1992.
Nabel et al., *Science*, 244(4910):1342-1344, 1989.
Naldini et al., *Science*, 272(5259):263-267, 1996.
Neish, *Inflamm. Bowel Dis.*, 10:159-168, 2004.
Nicolas and Rubinstein, In: *Vectors: A survey of molecular cloning vectors and their uses*, Rodriguez and Denhardt, eds., Stoneham: Butterworth, pp. 494-513, 1988.
Nicolau and Sene, *Biochim. Biophys. Acta*, 721:185-190, 1982.
Nicolau et al., *Methods Enzymol.*, 149:157-176, 1987.
Omirulleh et al., *Plant Mol. Biol.*, 21(3):415-428, 1993.
Otte and Podolsky, *Am. J. Physiol. Gastrointest. Liver Physiol.*, 286:G613-26, 2004.
Paskind et al., *Virology*, 67:242-248, 1975.
PCT Appln. WO 9217598
PCT Appln. WO 94/09699
PCT Appln. WO 94/09699
PCT Appln. WO 95/06128
Perales et al., *Proc. Natl. Acad. Sci. USA*, 91:4086-4090, 1994.
Potrykus et al., *Mol. Gen. Genet.*, 199(2):169-177, 1985.
Potter et al., *Proc. Natl. Acad. Sci. USA*, 81:7161-7165, 1984.
Reimund et al., *Eur. J. Clin. Invest.*, 28(2):145-150, 1998.
Remington's Pharmaceutical Sciences, 18th Ed. Mack Printing Company, 1289-1329, 1990.
Resta-Lenert and Barrett, *Gastroenterology*, 130:731-746, 2006.
Resta-Lenert and Barrett, *Gut.*, 52:988-997, 2003.
Rhodes et al., *Methods Mol. Biol.*, 55:121-131, 1995.
Ridgeway, In: *Vectors: A Survey of Molecular Cloning Vectors and Their Uses*, Rodriguez et al. (Eds.), Stoneham: Butterworth, 467-492, 1988.
Rippe, et al., *Mol. Cell Biol.*, 10:689-695, 1990.
Rogler and Andus, *World J. Surg.*, 22(4):382-389, 1998.
Roux et al., *Proc. Natl. Acad. Sci. USA*, 86:9079-9083, 1989.
Ruemmele et al., *Gastroenterol.*, 115(4):822-829, 1998.
Saiki et al., *Scand. J. Gastroenterol.*, 33(6):616-622, 1998.
Sambrook et al., In: *Molecular cloning: a laboratory manual*, $2^{nd}$ Ed., Cold Spring Harbor Laboratory Press, Cold Spring Harbor, N.Y., 1989.
Sartor, *Am. J. Gastroenterol.*, 92(12):5S-11S, 1997.
Sartor, *Gastroenterology*, 126:1620-1633, 2004.

Sartor, In: *Sleisenger & Fordtran's gastrointestinal and liver disease: pathophysiology, diagnosis, management*, Feldman et al. (Eds.), 7th Ed., 1:21-51, Saunders, Philadelphia, 2002.
Schreiber, *Neth. J. Med.*, 53(6):524-31, 1998.
Schultz et al., *BMC Gastroenterol.*, 4:5, 2004.
Sheng et al., *Gut.*, 52:1472-1478, 2003.
Sinha et al., *N. Engl. J. Med.*, 349:350-357, 2003.
Soderholm et al., *Gastroenterol.*, 117:65-72, 1999.
Stack et al., *Lancet.*, 349(9051):521-524, 1997.
Tao et al., *Am. J. Physiol. Cell Physiol.*, 290:C1018-1030, 2006.
Targan et al., *N. Engl. J. Med.*, 337(15):1029-1035, 1997.
Temin, In: *Gene Transfer*, Kucherlapati (Ed.), NY, Plenum Press, 149-188, 1986.
Tien et al., *J. Immunol.*, 176:1228-1237, 2006.
Tratschin et al., *Mol. Cell. Biol.*, 4:2072-2081, 1984.
Trencia et al., *Mol. Cell Biol.*, 23:4511-4521, 2003.
Tsukada et al., *Plant Cell Physiol.*, 30(4)599-604, 1989.
Tur-Kaspa et al., *Mol. Cell Biol.*, 6:716-718, 1986.
van Dullemen et al., *Gastroenterol.*, 109(1):129-135, 1995.
van Engeland et al., *Cytometry*, 31:1-9, 1998.
van Hogezand and Verspaget, *Drugs*, 56(3):299-305, 1998.
Vita et al., *Biopolymers* 47:93-100, 1998.
Wagner et al., *Proc. Natl. Acad. Sci. USA* 87(9):3410-3414, 1990.
Weisshoff et al., *Eur. J. Biochem.*, 259(3):776-788, 1999.
Wilson et al., *Science*, 244:1344-1346, 1989.
Wong et al., *Gene*, 10:87-94, 1980.
Wu and Wu, *Adv. Drug Delivery Rev.*, 12:159-167, 1993.
Wu and Wu, *Biochemistry*, 27: 887-892, 1988.
Wu and Wu, *J. Biol. Chem.*, 262:4429-4432, 1987.
Xu et al., *Science*, 299:2074-2076, 2003.
Yan and Polk, *Curr. Op. Gastroenterol.*, 20:565-571, 2004.
Yan and Polk, *J. Biol. Chem.*, 277:50959-50965, 2002.
Yan et al., *Cancer Res.*, 61:8668-8675, 2001.
Yan et al., *J. Clin. Invest.*, 114:1272-1280, 2004.
Yang and Russell, *Proc. Natl. Acad. Sci. USA*, 87:4144-4148, 1990.
Zeissig et al., *Gut.*, 53:1295-1302, 2004.
Zhang et al., *J. Clin. Invest.*, 115:2855-2861, 2005.
Zhou et al., *Nature*, 361(6412):543-547, 1993.
Zufferey et al., *Nat. Biotechnol.*, 15(9):871-875, 1997.

What is claimed is:

1. A method of inhibiting cytokine-induced epithelial cell apoptosis and/or promoting epithelial cell growth in a subject comprising administering to said subject a pharmaceutical composition comprising:
   (i) a purified and isolated protein having the properties of
      (a) stimulates PI3K-dependent Akt activation;
      (b) inhibits cytokine-induced epithelial cell apoptosis;
      (c) promotes epithelial cell growth;
      (d) an apparent molecular weight of 40 or 75 kDa as determined by SDS-PAGE;
      (e) a purity of 90%;
      (f) being a *Lactobacillus* protein, and
   (ii) a pharmaceutically acceptable buffer, diluent or excipient.

2. The method of claim 1, wherein the protein has an apparent molecular weight of 40 kDa.

3. The method of claim 1, wherein the protein has an apparent molecular weight of 75 kDa.

4. The method of claim 2, wherein the protein comprises the sequence of SEQ ID NO: 2.

5. The method of claim 3, wherein the protein comprises the sequence of SEQ ID NO: 4.

6. The method of claim 1, wherein said subject is a human, a rat, a mouse, a sheep, a dog, a cat, a rabbit.

7. The method of claim 1, wherein said subject suffers from a gastrointestinal infection.

8. The method of claim 7, wherein said gastrointestinal infection comprises cholera, rotavirus infection or infection by enterotoxigenic *E. coli*.

9. The method of claim 1, wherein said subject suffers from a gastrointestinal disorder.

10. The method of claim 9, wherein said gastrointestinal disorder comprises inflammatory bowel disease, irritable bowel syndrome, Crohn's disease, necrotizing enterocolitis, ulcerative colitis, celiac disease, HIV enteropathy, *Helicobacter* gastritis or NSAID-enteropathy/enteritis.

11. The method of claim 1, wherein said epithelial cell is comprised within skin tissue, corneal tissue or lung tissue.

12. The method of claim 11, wherein said epithelial cell is comprised within an inflamed tissue.

13. The method of claim 1, wherein said epithelial cell is comprised within heart tissue, muscle or a joint.

14. The method of claim 13, wherein said epithelial cell is comprised within cytokine-injured tissue.

15. The method of claim 1, wherein the protein has a purity of 95%.

16. The method of claim 1, wherein the protein has a purity of 99%.

* * * * *

UNITED STATES PATENT AND TRADEMARK OFFICE
CERTIFICATE OF CORRECTION

PATENT NO. : 9,682,120 B2
APPLICATION NO. : 14/833611
DATED : June 20, 2017
INVENTOR(S) : D. Brent Polk et al.

Page 1 of 1

It is certified that error appears in the above-identified patent and that said Letters Patent is hereby corrected as shown below:

In the Specification

In Column 1, Lines 17-20, please delete the paragraph and insert:
--This invention was made with government support under Grant Nos. DK056008, DK058404, DK065744, and DK065788, awarded by the National Institutes of Health. The government has certain rights in the invention.-- therefor.

Signed and Sealed this
Twenty-sixth Day of September, 2023

Katherine Kelly Vidal
*Director of the United States Patent and Trademark Office*

SEQUENCE LISTING

```
<160> NUMBER OF SEQ ID NOS: 4

<210> SEQ ID NO 1
<211> LENGTH: 1239
<212> TYPE: DNA
<213> ORGANISM: Lactobacillus acidophilus

<400> SEQUENCE: 1
atgaaattca ataaagcaat gatcacgttg gttgctgcag ttaccttagc gggttctgtt      60
agcgccttaa caccggtttt cgctgacaca agtgccagca tcgcatctaa caagagcgaa     120
accaacgatt tattaaagca aatcgaagca gctaacactg aagtgatcaa cctcaacaaa     180
cagattgatg ctaagaatgg cgaaatcagt gacgccactg ccaagatcag tgcaacggat     240
gccaagatcg catcgttgag tggcgaaatc accgctgctc aaaagaacgt cgcagcccgg     300
aagaacaact tgaaggatca attgatttcc cttcaaaaga aagccggcag ttcagttagc     360
ggcaatgtct atattgattt cgtgttgaac tcacaaagtc tatctgactt gattgcccgt     420
accatgacag tcggcaagtt aagtcaagcc agcaaagacg ctttggatgc ggtaaccgtc     480
gccaaagata agttagccgc tttgaagagt gaacaggaaa cggcacgtca gaccttggtt     540
tcgactaaag catctcttga aacgcaaaag tcacagctag agaccttca aaagaccgca     600 agcgataagc aagatgcttt gaacaaagaa attgctgatc acaaagacga attggttgca     660
ctccaaagtc aatttgctca agaacaatca gaagcagcca aagcaaccca ggctgccttg     720
aagacagcag ctgcatcaac tgcttcaagt tctaccagct caacttcaaa taagagtgcc     780
aacagcagtg ttctttcgac tggtacctca tcaaccaaca cttcttccaa cagcggtgcc     840
tcatctactg tgatcagcag caacactgct tcaggtagcg gcagccatgc tgattacagc     900
ggttcaggta acacttatcc ttggggtcag tgcacatggt acgttaagtc tgttgcttca     960
tgggcaggca atggctgggg caacggtgct gaatggggcg cttccgctgc agcagccggc    1020
ttcacggtta accacacccc ggcagcaggt tccatcatcg tcttcgctgc tggtcaatct    1080
gttggcggcc aatggacagc tgatggctct tatggtcacg ttgcttatgt tcaatctgtt    1140 tctgcgaca gcgttacgat cactcaaggc ggcatgggct tcagctcacc aaccggtcct    1200
aacacccaga ccatctctgg tgccagcagc tacgtttaa                          1239
```

<210> SEQ ID NO 2
<211> LENGTH: 412
<212> TYPE: PRT
<213> ORGANISM: Lactobacillus acidophilus

<400> SEQUENCE: 2

```
Met Lys Phe Asn Lys Ala Met Ile Thr Leu Val Ala Ala Val Thr Leu
1               5                   10                  15

Ala Gly Ser Val Ser Ala Leu Thr Pro Val Phe Ala Asp Thr Ser Ala
            20                  25                  30

Ser Ile Ala Ser Asn Lys Ser Glu Thr Asn Asp Leu Leu Lys Gln Ile
        35                  40                  45

Glu Ala Ala Asn Thr Glu Val Ile Asn Leu Asn Lys Gln Ile Asp Ala
50                  55                  60

Lys Asn Gly Glu Ile Ser Asp Ala Thr Ala Lys Ile Ser Ala Thr Asp
65                  70                  75                  80

Ala Lys Ile Ala Ser Leu Ser Gly Glu Ile Thr Ala Ala Gln Lys Asn
                85                  90                  95

Val Ala Ala Arg Lys Asn Asn Leu Lys Asp Gln Leu Ile Ser Leu Gln
            100                 105                 110

Lys Lys Ala Gly Ser Ser Val Ser Gly Asn Val Tyr Ile Asp Phe Val
        115                 120                 125

Leu Asn Ser Gln Ser Leu Ser Asp Leu Ile Ala Arg Thr Met Thr Val
130                 135                 140

Gly Lys Leu Ser Gln Ala Ser Lys Asp Ala Leu Asp Ala Val Thr Val
145                 150                 155                 160

Ala Lys Asp Lys Leu Ala Ala Leu Lys Ser Glu Gln Glu Thr Ala Arg
                165                 170                 175

Gln Thr Leu Val Ser Thr Lys Ala Ser Leu Glu Thr Gln Lys Ser Gln
            180                 185                 190

Leu Glu Thr Leu Gln Lys Thr Ala Ser Asp Lys Gln Asp Ala Leu Asn
        195                 200                 205

Lys Glu Ile Ala Asp His Lys Asp Glu Leu Val Ala Leu Gln Ser Gln
210                 215                 220

Phe Ala Gln Glu Gln Ser Glu Ala Ala Lys Ala Thr Gln Ala Ala Leu
225                 230                 235                 240

Lys Thr Ala Ala Ala Ser Thr Ala Ser Ser Thr Ser Ser Thr Ser
                245                 250                 255

Asn Lys Ser Ala Asn Ser Ser Val Leu Ser Thr Gly Thr Ser Ser Thr
            260                 265                 270

Asn Thr Ser Ser Asn Ser Gly Ala Ser Ser Thr Val Ile Ser Ser Asn
        275                 280                 285

Thr Ala Ser Gly Ser Gly Ser His Ala Asp Tyr Ser Gly Ser Gly Asn
290                 295                 300

Thr Tyr Pro Trp Gly Gln Cys Thr Trp Tyr Val Lys Ser Val Ala Ser
305                 310                 315                 320

Trp Ala Gly Asn Gly Trp Gly Asn Gly Ala Glu Trp Gly Ala Ser Ala
                325                 330                 335

Ala Ala Ala Gly Phe Thr Val Asn His Thr Pro Ala Ala Gly Ser Ile
            340                 345                 350

Ile Val Phe Ala Ala Gly Gln Ser Val Gly Gly Gln Trp Thr Ala Asp
        355                 360                 365

Gly Ser Tyr Gly His Val Ala Tyr Val Gln Ser Val Ser Gly Asp Ser
```

```
                370               375               380
Val Thr Ile Thr Gln Gly Gly Met Gly Phe Ser Ser Pro Thr Gly Pro
385               390               395               400

Asn Thr Gln Thr Ile Ser Gly Ala Ser Ser Tyr Val
            405               410

<210> SEQ ID NO 3
<211> LENGTH: 1488
<212> TYPE: DNA
<213> ORGANISM: Lactobacillus acidophilus

<400> SEQUENCE: 3
atggtagatt ctaagaaagt attgtcagta acggcaggct tcgttggtgc tgccggtctg      60
gcggctttag caaccggagc caataccgtt tctgcatcga cagggacggt cagttacaaa     120
tccggtgcga ccaccgtatg gaatagtcca tcatggcacc aagtcaaacg ctacgtgact     180
tttggggaca cggtgcagct attgggtaaa accgttgacc aaaatggtgc tacttggtat     240
aaagttggcg acaatcagtg gattccggaa ttgtatttga atgttgcggg taaaactgcc     300
acggttgaaa caccgagttc ggcagcaagt caaactgctg tcagccaagc accggctagt     360
caggcgccta aagccaagc accagcaacc caaacacctg cagcaccaca aaccgatacc     420
caaacagcta atacacagct ttatgtcaag aatatcggtt cagcagttac cgtatggaca     480
accccggcgt atactcatgc gacaggtcaa tatctagaag cagccagac actgacggct     540 gttgcccagc agcaagcaaa tggtgaaaca tggtatcggc ttgccaacgg cggttatgtt     600
cctgcacggt tgttacacaa caccagtggc tgtaacacca caactgcagc gccacagtca     660
aatgaggcca gtgttgcgtc aacgaacacc aatgcagcta atgattctgc cgctgcttct     720
agtgcagccg catcgcaagc cgcagcttcc agtgctgccg cttctacagc agcagctaat     780
gcagcagtag catctgcaaa tgccactgca tcacaagcag cggcttctga agctgctgca     840
tctcaggcgc tgcatcaca agccgcagcg tctcaggctg ccgcatcgca agccgcagca     900
tcacaagctg cagcgtctca ggcggctgca tcacaagccg ccgcttcaca agctgcagcg     960
tcccaggctg ccgcatcaca agcagctgca aatgctgccc agcaggcgcc ggctaaccag    1020
gcaaatgtta caacaacaca ggttaatgcc aatcaagctc aacagcaaac cgctacggct    1080
acaccagcag ttaacacgtc taatcagacg gcggccgtaa gtgcttcaag acaggccaag    1140
attcaagcag tgattgccat tgccgaacaa caagttggta agccatacgt ttggggcggt    1200
aaggggccta acagctttga ttgctccggt tgatgtatt acgctttcct gaatggcgct    1260
ggcgtcaaca ttggtggctg acagttcct caagaatctt cagggacaca gtttcactg     1320 agtgctctgc aacccggtga cttactcttc tggggtagtc acggttcaac ctatcacgtt    1380
gccctgtaca tcggtggcgg cacgatgatt caggcgccac agccaggtga aaatgttaaa    1440
tataccgcgc tggcatactt catgcctgat tgctgttcg tccttcac                  1488

<210> SEQ ID NO 4
<211> LENGTH: 496
<212> TYPE: PRT
<213> ORGANISM: Lactobacillus acidophilus

<400> SEQUENCE: 4

Met Val Asp Ser Lys Lys Val Leu Ser Val Thr Ala Gly Phe Val Gly
1               5                   10                  15

Ala Ala Gly Leu Ala Ala Leu Ala Thr Gly Ala Asn Thr Val Ser Ala
            20                  25                  30
```

```
Ser Thr Gly Thr Val Ser Tyr Lys Ser Gly Ala Thr Thr Val Trp Asn
        35                  40                  45

Ser Pro Ser Trp His Gln Val Lys Arg Tyr Val Thr Phe Gly Asp Thr
50                  55                  60

Val Gln Leu Leu Gly Lys Thr Val Asp Gln Asn Gly Ala Thr Trp Tyr
65                  70                  75                  80

Lys Val Gly Asp Asn Gln Trp Ile Pro Glu Leu Tyr Leu Asn Val Ala
                85                  90                  95

Gly Lys Thr Ala Thr Val Glu Thr Pro Ser Ser Ala Ala Ser Gln Thr
                100                 105                 110

Ala Val Ser Gln Ala Pro Ala Ser Gln Ala Pro Thr Ser Gln Ala Pro
                115                 120                 125

Ala Thr Gln Thr Pro Ala Ala Pro Gln Thr Asp Thr Gln Thr Ala Asn
                130                 135                 140

Thr Gln Leu Tyr Val Lys Asn Ile Gly Ser Ala Val Thr Val Trp Thr
145                 150                 155                 160

Thr Pro Ala Tyr Thr His Ala Thr Gly Gln Tyr Leu Glu Gly Ser Gln
                165                 170                 175

Thr Leu Thr Ala Val Ala Gln Gln Gln Ala Asn Gly Glu Thr Trp Tyr
                180                 185                 190

Arg Leu Ala Asn Gly Gly Tyr Val Pro Ala Arg Leu Leu His Asn Thr
                195                 200                 205

Ser Gly Cys Asn Thr Thr Thr Ala Ala Pro Gln Ser Asn Glu Ala Ser
                210                 215                 220

Val Ala Ser Thr Asn Thr Asn Ala Ala Asn Asp Ser Ala Ala Ala Ser
225                 230                 235                 240

Ser Ala Ala Ala Ser Gln Ala Ala Ala Ser Ser Ala Ala Ala Ser Thr
                245                 250                 255

Ala Ala Ala Asn Ala Ala Val Ala Ser Ala Asn Ala Thr Ala Ser Gln
                260                 265                 270

Ala Ala Ala Ser Glu Ala Ala Ala Ser Gln Ala Ala Ala Ser Gln Ala
                275                 280                 285

Ala Ala Ser Gln Ala Ala Ala Ser Gln Ala Ala Ala Ser Gln Ala Ala
                290                 295                 300

Ala Ser Gln Ala Ala Ala Ser Gln Ala Ala Ala Ser Gln Ala Ala Ala
305                 310                 315                 320

Ser Gln Ala Ala Ala Ser Gln Ala Ala Ala Asn Ala Ala Gln Gln Ala
                325                 330                 335

Pro Ala Asn Gln Ala Asn Val Thr Thr Thr Gln Val Asn Ala Asn Gln
                340                 345                 350

Ala Gln Gln Gln Thr Ala Thr Ala Thr Pro Ala Val Asn Thr Ser Asn
                355                 360                 365

Gln Thr Ala Ala Val Ser Ala Ser Arg Gln Ala Lys Ile Gln Ala Val
                370                 375                 380

Ile Ala Ile Ala Glu Gln Gln Val Gly Lys Pro Tyr Val Trp Gly Gly
385                 390                 395                 400

Lys Gly Pro Asn Ser Phe Asp Cys Ser Gly Leu Met Tyr Tyr Ala Phe
                405                 410                 415

Leu Asn Gly Ala Gly Val Asn Ile Gly Gly Trp Thr Val Pro Gln Glu
                420                 425                 430

Ser Ser Gly Thr Gln Val Ser Leu Ser Ala Leu Gln Pro Gly Asp Leu
                435                 440                 445
```

-continued

```
Leu Phe Trp Gly Ser His Gly Ser Thr Tyr His Val Ala Leu Tyr Ile
    450             455             460

Gly Gly Gly Thr Met Ile Gln Ala Pro Gln Pro Gly Glu Asn Val Lys
465             470             475             480

Tyr Thr Ala Leu Ala Tyr Phe Met Pro Asp Leu Leu Phe Val Leu His
            485             490             495
```